United States Patent
Roden et al.

(10) Patent No.: US 12,410,141 B2
(45) Date of Patent: Sep. 9, 2025

(54) ANTI-CANCER SPIROCYCLIC-GUANIDINE COMPOUNDS AND USES THEREOF

(71) Applicant: The Johns Hopkins University, Baltimore, MD (US)

(72) Inventors: Richard B. S. Roden, Baltimore, MD (US); Ravi K. Anchoori, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 512 days.

(21) Appl. No.: 17/925,923

(22) PCT Filed: May 18, 2021

(86) PCT No.: PCT/US2021/032982
§ 371 (c)(1),
(2) Date: Nov. 17, 2022

(87) PCT Pub. No.: WO2021/236654
PCT Pub. Date: Nov. 25, 2021

(65) Prior Publication Data
US 2023/0242488 A1 Aug. 3, 2023

Related U.S. Application Data

(60) Provisional application No. 63/026,268, filed on May 18, 2020.

(51) Int. Cl.
*C07D 221/20* (2006.01)
*A61P 35/00* (2006.01)

(52) U.S. Cl.
CPC .......... *C07D 221/20* (2013.01); *A61P 35/00* (2018.01)

(58) Field of Classification Search
CPC .................................................. C07D 221/20
See application file for complete search history.

(56) References Cited

U.S. PATENT DOCUMENTS 9,913,834 B2  3/2018  Roden et al.
2013/0296354 A1 11/2013 Eckhardt

FOREIGN PATENT DOCUMENTS

WO  2018/140907  8/2018
WO  2019/035927  2/2019

OTHER PUBLICATIONS

Budenholzer et al., "Proteasome Structure and Assembly", J Mol Biol., (2017), vol. 429, pp. 3500-3524.
Collins et al., "The Logic of the 26S Proteasome", Cell, (2017), vol. 169, pp. 792-806.
Cromm et al., "The Proteasome in Modern Drug Discovery: Second Life of a Highly Valuable Drug Target", ACS Cent Sci., (2017), vol. 3, pp. 830-838.
Xi et al., "Immunoproteasome-selective inhibitors: An overview of recent developments as potential drugs for hematologic malignancies and autoimmune diseases", Eur J Med Chem., (2019), vol. 182, 111646, (17 pages).
Bazzaro et al., "Ubiquitin-proteasome system stress sensitizes ovarian cancer to proteasome inhibitor-induced apoptosis", Cancer Res., (2006), vol. 66, pp. 3754-3763.
Yu et al., "Differential apoptotic response to the proteasome inhibitor Bortezomib [VELCADE, PS-341] in Bax-deficient and p21-deficient colon cancer cells", Cancer Biol Ther., (2003), vol. 2, pp. 694-699.
Petrocca et al., "A genome-wide siRNA screen identifies proteasome addiction as a vulnerability of basal-like triple-negative breast cancer cells", Cancer Cell, (2013), vol. 24, pp. 182-196.
Tsvetkov et al., "Oncogenic addiction to high 26S proteasome level", Cell Death Dis., (2018), vol. 9, 773, (14 pages).
Parma et al., "An open-label phase 2 study of twice-weekly bortezomib and intermittent pegylated liposomal doxorubicin in patients with ovarian cancer failing platinum-containing regimens", Int J Gynecol Cancer, (2012), vol. 22, pp. 792-800.
Adelson et al., "Randomized phase II trial of fulvestrant alone or in combination with bortezomib in hormone receptor-positive metastatic breast cancer resistant to aromatase inhibitors: a New York Cancer Consortium trial", NPJ Breast Cancer, (2016), vol. 2, 16037, (6 pages).
Pugh et al., "Phase I trial of bortezomib and concurrent external beam radiation in patients with advanced solid malignancies", Int J Radiat Oncol Biol Phys., (2010), vol. 78, No. 2, pp. 521-526.
Gilbert et al., "Phase II 2-arm trial of the proteasome inhibitor, PS-341 (bortezomib) in combination with irinotecan or PS-341 alone followed by the addition of irinotecan at time of progression in patients with locally recurrent or metastatic squamous cell carcinoma of the head and neck (E1304): a trial of the Eastern Cooperative Oncology Group", Head Neck, (2013), vol. 35, pp. 942-948.
Jandial et al., "A phase I pharmacokinetic study of intraperitoneal bortezomib and carboplatin in patients with persistent or recurrent ovarian cancer: An NRG Oncology/Gynecologic Oncology Group study", Gynecol Oncol., (2017), vol. 145, pp. 236-242.

(Continued)

*Primary Examiner* — Nizal S Chandrakumar
(74) *Attorney, Agent, or Firm* — Venable LLP; Keith G. Haddaway; Hemant Khanna

(57) ABSTRACT

The invention of the instant application discloses spirocyclic guanidine compounds of general formula (I), shown below, and their use in methods of treating cancer

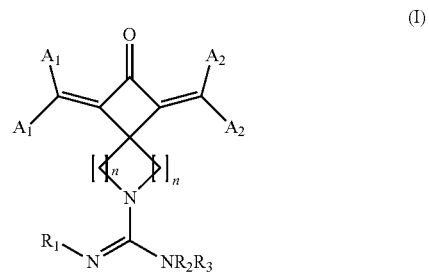

(I)

4 Claims, 10 Drawing Sheets

(56) References Cited

OTHER PUBLICATIONS

Roeten et al., "Positioning of proteasome inhibitors in therapy of solid malignancies", Cancer Chemother Pharmacol., (2018), vol. 81, pp. 227-243.
Dou et al., "Overview of proteasome inhibitor-based anti-cancer therapies: perspective on bortezomib and second generation proteasome inhibitors versus future generation inhibitors of ubiquitin-proteasome system", Curr Cancer Drug Targets, (2014), vol. 14, pp. 517-536.
Shi et al., "Rpn1 provides adjacent receptor sites for substrate binding and deubiquitination by the proteasome", Science, (2016), vol. 351. (12 pages).
Elsasser et al., "Rad23 and Rpn10 serve as alternative ubiquitin receptors for the proteasome", J Biol Chem., (2004), vol. 279, No. 26, pp. 26817-26822.
Husnjak et al., "Proteasome subunit Rpn13 is a novel ubiquitin receptor", Nature, (2008), vol. 453, pp. 481-488.
Lu et al., "An Extended Conformation for K48 Ubiquitin Chains Revealed by the hRpn2:Rpn13:K48-Diubiquitin Structure", Structure, (2020), vol. 28, pp. 495-506.
Cundiff et al., "Ubiquitin receptors are required for substrate-mediated activation of the proteasome's unfolding ability", Sci Rep., (2019), vol. 9, 14506.
Martinez-Fonts et al., "The proteasome 19S cap and its ubiquitin receptors provide a versatile recognition platform for substrates", Nat Commun., (2020), vol. 11, 477.
Chen et al., "Structural plasticity allows UCH37 to be primed by RPN13 or locked down by INO80G", Mol Cell, (2015), vol. 57, pp. 767-768.
VanderLinden et al., "Structural basis for the activation and inhibition of the UCH37 deubiquitylase", Mol Cell, (2015), vol. 57, pp. 901-911.
Jiao et al., "Mechanism of the Rpn13-induced activation of Uch37", Protein Cell, (2014), vol. 5, pp. 616-630.
VanderLinden et al., "Structure and energetics of pairwise interactions between proteasome subunits RPN2, RPN13, and ubiquitin clarify a substrate recruitment mechanism", J Biol Chem., (2017), vol. 292, pp. 9493-9504.
Chen et al., "Structure of proteasome ubiquitin receptor hRpn13 and its activation by the scaffolding protein hRpn2", Mol Cell, (2010), vol. 38, pp. 404-415.
Hemmis et al., "Phosphorylation of Tyr-950 in the proteasome scaffolding protein RPN2 modulates its interaction with the ubiquitin receptor RPN13", J Biol Chem., (2019), vol. 294, pp. 9659-9665.
Lu et al., "A High Affinity hRpn2-Derived Peptide That Displaces Human Rpn13 from Proteasome in 293T Cells", PLoS One, (2015), vol. 10, No. 10, e0140518, (13 pages).
Besche et al., "Autoubiquitination of the 26S proteasome on Rpn13 regulates breakdown of ubiquitin conjugates" EMBO J. (2014), vol. 33, pp. 1159-1176.
Jiang et al., "Early and consistent overexpression of ADRM1 in ovarian high-grade serous carcinoma", J Ovarian Res., (2017), vol. 10:53, (12 pages).

Soong et al., "RPN13/ADRM1 inhibitor reverses immunosuppression by myeloid-derived suppressor cells", Oncotarget, (2016), vol. 7, No. 42, pp. 68489-68502.
Fejzo et al., "ADRM1-amplified metastasis gene in gastric cancer", Genes Chromosomes Cancer, (2015), vol. 54, pp. 506-515.
Jang et al., "ADRM1 gene amplification is a candidate driver for metastatic gastric cancers", Clin Exp Metastasis, (2014), vol. 31, pp. 727-733.
Anchoori et al., "A bis-benzylidine piperidone targeting proteasome ubiquitin receptor RPN13/ADRM1 as a therapy for cancer", Cancer Cell, (2013), vol. 24, pp. 791-805.
Kisselev "A novel bullet hits the proteasome", Cancer Cell, (2013), vol. 24, pp. 691-693.
Fejzo et al., "Amplification Target ADRM1: Role as an Oncogene and Therapeutic Target for Ovarian Cancer", Int J Mol Sci., (2013), vol. 14, pp. 3094-3109.
Hamazaki et al., "Redundant Roles of Rpn10 and Rpn13 in Recognition of Ubiquitinated Proteins and Cellular Homeostasis", PLoS Genet, (2015), vol. 11, No. 7, e1005401, (20 pages).
Al-Shami et al., "Regulators of the proteasome pathway, Uch37 and Rpn13, play distinct roles in mouse development", PLoS One, (2010), vol. 5, Issue 10, e13654, (11 pages).
Zheng et al., "Knockdown of Adhesion-Regulating Molecule 1 Inhibits Proliferation in HL60 Cells", Acta Haematol., (2015), vol. 134, pp. 88-100.
Fejzo et al., "Comprehensive analysis of 20q13 genes in ovarian cancer identifies ADRM1 as amplification target", Genes Chromosomes Cancer, (2008), vol. 47, pp. 873-883.
Baell et al., "Seven Year Itch: Pan-Assay Interference Compounds (PAINS) in 2017-Utility and Limitations", ACS Chem Biol., (2018), vol. 13, pp. 36-44.
Lagorce et al., "Pan-assay interference compounds (PAINS) that may not be too painful for chemical biology projects". Drug Discov Today, (2017), vol. 22, No. 8, pp. 1131-1133.
Rowinsky et al., "Phase 1 study of the protein deubiquitinase inhibitor VLX1570 in patients with relapsed and/or refractory multiple myeloma", Invest New Drugs, (2020), vol. 38, pp. 1448-1453.
Zheng et al., "The utilization of spirocyclic scaffolds in novel drug discovery", Expert Opin Drug Discov., (2016), vol. 11, No. 9, pp. 831-834.
Muller et al., "Charting Biologically Relevant Spirocyclic Compound Space", Chemistry, (2017), vol. 23, pp. 703-710.
Luker et al., "Imaging 26S proteasome activity and inhibition in living mice", Nat Med., (2003), vol. 9, No. 7, pp. 969-973.
Daina et al., "SwissADME: a free web tool to evaluate pharmacokinetics, drug-likeness and medicinal chemistry friendliness of small molecules", Sci Rep., (2017), vol. 7, 42717, (13 pages).
Yang et al., "Badapple: promiscuity patterns from noisy evidence", J Cheminform, (2016), vol. 8, 29, (14 pages).
Dahlin et al., "How to Triage PAINS—Full Research", Assay Drug Dev Technol., (2016), vol. 14, pp. 168-174.
Anchoori et al., "Covalent Rpn13-Binding Inhibitors for the Treatment of Ovarian Cancer", ACS Omega, vol. 3, No. 9, Sep. 27, 2018 (Sep. 27, 2018), pp. 11917-11929.
Pubmed Compound Record for CID 135275374, '(1 E,3E)-1,3-Bis[(4-chlorophenyl)methylidene]-7-prop-2-enoyl-7-azaspiro[3.4]octan-2-one', U.S. National Library of Medicine, Dec. 15, 2018 (Dec. 15, 2018), pp. 1-8 (https://pubchem.nobi.nlm.nih.gov/compound/135275374 ); p. 2.

(a) 4-CN-Ph-CHO, Ethanol, 0°C-rt, 30 min (b) 4M HCl in dioxane, rt, 30 min (c) Et₃N, Acetonitrile, N, N'-Bis-Boc-1-guanylpyrazole, 50C 12h (d) 4M HCl in dioxane

ANTI-CANCER SPIROCYCLIC-GUANIDINE COMPOUNDS AND USES THEREOF

PRIORITY

This application is a U.S. National Stage of PCT/US2021/032982, filed May 18, 2021, which claims priority to U.S. provisional application 63/026,268 filed May 18, 2020, which the entire contents thereof are incorporated by reference.

U.S. GOVERNMENT SUPPORT

This invention was made with Government support under grant numbers CA098252, CA228991, CA006973 from the National Institutes of Health, National Cancer Institute. The government has certain rights in this invention.

BACKGROUND OF THE INVENTION

Area of the Art

The present invention relates to a class of novel spirocyclic-guanidine molecules and can be used as therapeutic agents against various types of cancers. Specifically, these molecules work as proteasome inhibitors and bind to the RPN13 subunit of the 19S regulatory particle.

Description of the Background Art

The constitutively-expressed 26S proteasome is a large multi-subunit complex which mediates targeted degradation of the majority of proteins within the cell under normal conditions to regulate cellular processes, eliminate aberrantly folded polypeptides, and to maintain proteostasis (1, 2). The 26S proteasome compromises two subcomplexes: the 20S core particle (20S CP) with three distinct proteolytic activities, and the 19S regulatory particle (19S RP) controlling which substrates are fed in an ATP-dependent manner into the 20S CP for degradation. Selective covalent attachment of the 8.5 kDa ubiquitin tag, typically in chains linked by K48, to a protein substrate is recognized by the 19S RP and targets it for proteasomal degradation.

The FDA has approved three proteasome inhibitors (PIs), bortezomib/Velcade, carfilzomib/Kyprolis, and ixazomib/Ninlaro, for the treatment of multiple myeloma (MM), and others are in advanced clinical trials, e.g. oprozomib and marizomib. All of these PIs are covalent inhibitors of the chymotrypsin-like activity within the 20S CP's PSMB5 subunit, while generally sparing the caspase-like and trypsin-like activities of PSMB1 and PSMB2 respectively (3). In contrast, the immunoproteasome is expressed predominantly in monocytes and lymphocytes and has distinct, but related, catalytic subunits in its 20S CP, and an 11S cap that permits substrate degradation independently of either ATP or ubiquitin.

The immunoproteasome functions to generate substrate epitopes for the antigen presentation by major histocompatibility complex class I (MHCI) receptors and induction of cellular immunity. Several licensed PIs also inhibit the immunoproteasome, and immunoproteasome-specific inhibitors are in development to treat autoimmune diseases (4).

The licensed peptide-based PIs have greatly improved the prognosis of MM patients and thereby validated the proteasome as an anticancer drug target. Furthermore, they exhibited promising in vitro activity against a number of cell lines derived from solid cancers, especially ovarian (5), colon (6) and triple negative breast cancer (7, 8). However, in early phase clinical trials these drugs were insufficiently effective against solid tumors to warrant further development (9-12). This has been attributed to poor drug penetration as a reflection of their peptide-based backbone, and their short half-life in vivo (13, 14). The dose window is limited by off-target neurotoxicity, notably peripheral neuropathy, and thrombocytopenia. Finally, prolonged treatment of MM patients with the licensed proteasome inhibitors is associated with the development of resistance and progression (15). To overcome these limitations, a new class of proteasome inhibitors with a distinct mechanism of action and molecular scaffold have been developed.

Three 19S RP subunits, RPN1 (16), RPN10 (17), and RPN13 (18), have been identified as ubiquitin receptors which mediate the recognition of polyubiquitinated substrate proteins. In preparation for degradation, the ubiquitin tag(s) are cleaved off 19S RP-bound substrates by three deubiquitinases, RPN11, USP14 and UCH37, prior to substrate unfolding and their translocation to the 20S CP. The three ubiquitin receptors are required for substrate-mediated activation of unfolding by the proteasome. RPN13 plays the largest role and preferentially binds to extended K48-linked ubiquitin chains (19). While there is also partial redundancy between receptors (20), they provide a versatile binding platform to recognize substrates targeted for degradation by ubiquitin chains differing greatly in length and topology (21).

RPN13 also binds to UCH37, and this interaction activates UCH37's deubiquitinase function (22, 23) by revealing the active site (24). RPN13 binds to the 19S RP via interaction with the C-terminal 14 amino acids of the RPN2 subunit (25), and this abrogates the association of RPN13's ubiquitin (PRU) and UCH37 binding (DEUBAD) domains, enhancing its affinity for ubiquitin (26). Phosphorylation of Y950 of RPN2 enhances binding of RPN13, suggesting regulation of this interaction (27). Overexpression of the C-terminal RPN2 peptide displaces RPN13 off the proteasome, resulting in the accumulation of polyubiquinated proteins in the cell and supporting its role as the primary binding site for RPN13 (28). RPN13 function is also regulated by ubiquitination which strongly decreases the proteasome's ability to bind and degrade ubiquitin-conjugated proteins (29).

RPN13, which is encoded by the ADRM1 gene, has emerged as a promising target for the treatment of ovarian cancer and several other types of solid tumors (30-36). RPN13 was found non-essential for the survival of normal cells (37) and even mice (38) suggesting that it might be safely targeted* with inhibitors. Importantly, RPN13 is critical in numerous cancer cell lines, including cells from solid tumors (30, 39, 40), and ADRM1 has been proposed as a driver oncogene in ovarian cancer (36). RA190 is a prototypic small molecule inhibitor of RPN13 (iRPN13) (34).

U.S. Pat. No. 9,913,834, incorporated herein by reference, discusses RPN13 technology and RA190, shown below (and its biotinylated analog, RA190B, also shown below). This bis-benzylidine piperidone compound was found to covalently bind to the RPN13 receptor in the 19S regulatory particle and inhibit proteasome function, triggering rapid accumulation of polyubiquinated proteins. Possessing oral bioavailability, treatment with RA190 was highly effective against a multiple myeloma xenograft. RA190 also inhibited tumor growth in mice bearing model ovarian and cervical cancers, suggesting activity of this iRPN13 against solid tumors. RA190 was equivalently active against parental myeloma cell lines and those selected for resistance to bortezomib, implying a different mode of action and potential of iRPN13 for treatment of patients whose disease has become resistant to the licensed 20S proteasome inhibitors.

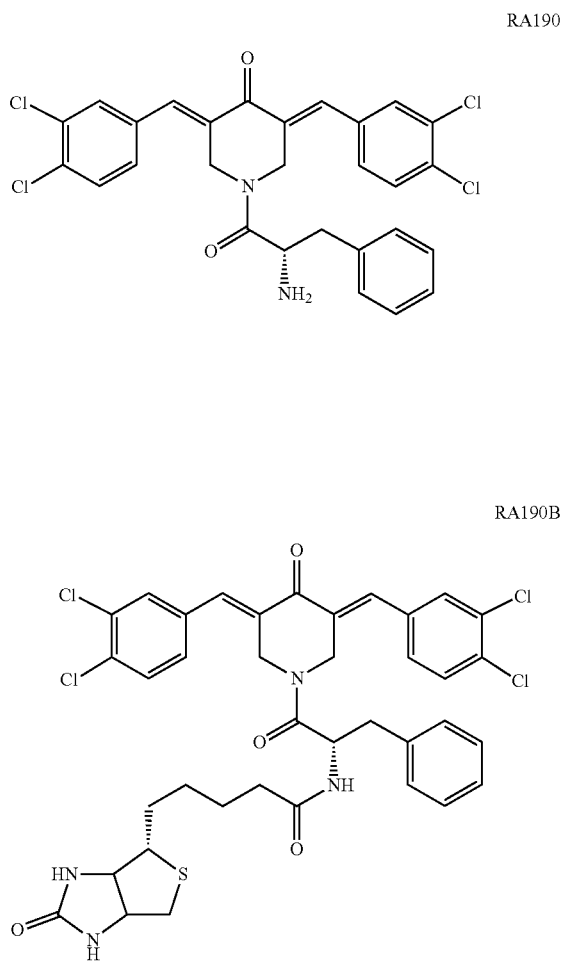

SUMMARY OF THE INVENTION

It was desired to develop an iRPN13 with more drug-like characteristics than RA190 with respect to removal of the Pan Assay INterference CompoundS (PAINS)-like backbone (41), improved solubility, safety and pharmaco-kinetics/dynamics. While 6-7% of approved drugs are flagged as PAINS and therefore this is not necessarily disqualifying (42), a related compound demonstrated severe pulmonary toxicity (43). One approach to avoid the bis-benzylidine-piperidone PAINS-like structure is to convert the backbone to a spiro-bis-benzylidine piperidone, as recently described in WO2018/140907A1 (also published as US PG Pub 2019-0365726 A1).

Indeed, given their structural novelty, spiro-scaffolds have been increasingly utilized in drug discovery (44, 45). The present invention discloses the design and synthesis of compounds based on the spiro-bis-benzylidine piperidone frame work for drug-likeness and their screening for their ability to bind to RPN13 in tumor cell lysates, to trigger the rapid accumulation of high molecular weight polyubiquitinated proteins and associated tumor cell death via apoptosis. Further, the iRPN13 should be well tolerated by the host, and provide inhibition of the proteasome with suitable pharmacokinetics on-target. Fortunately, for assessing the pharmacodynamics of on-target proteasome inhibition, an elegant reporter gene system comprising a tandem fusion of four ubiquitin to firefly luciferase (4UbFL) has been developed (46).

The spirocyclic-guanidine compounds of the invention have the general structure of formula (I) shown below:

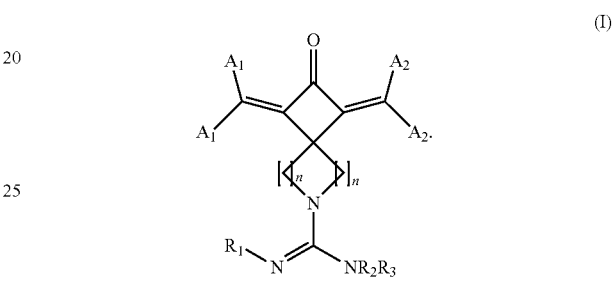

wherein at each occurrence n is an integer independently selected from 1-3;
wherein $R_2$ is $C(NR_1)NR_3R_3$, $R_1$, or $R_3$; or
wherein $R_1$ and $R_3$ together with the intervening atoms to which they are attached form a 5- or 6-membered heterocycle optionally substituted with one or more $R_1$ groups; or
wherein $R_2$ and $R_3$ together with the intervening atoms to which they are attached form a 5- or 6-membered heterocycle optionally substituted with one or more $R_1$ groups;
wherein each $R_1$ and $R_3$ may be the same or different and are selected from the following:
  i) hydrogen;
  ii) —$C_1$-$C_{14}$ linear, branched, or cyclic alkyl optionally substituted with halogen up to perhalo;
  iii) —$C_0$-$C_3$ alkyl-phenyl wherein the phenyl moiety is optionally substituted with 1-5 substituents selected from cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, and $OCF_3$, and wherein the alkyl moiety is optionally substituted with halogen up to perhalo;
  iv) —$C_0$-$C_4$-alkyl-K wherein K is a 5- or 6-membered monocyclic heterocyclic ring containing 1-4 atoms selected from O, N, and S, or an 8- to 10-membered bicyclic heteroaryl having 1-4 heteroatoms selected from O, N and S, and wherein said alkyl moiety is optionally substituted with halogen up to perhalo;
  v) —$C(O)R_4$; and
  vi) —$SO_2NR_4R_4$; and
wherein one occurrence of $A_1$ and one occurrence of $A_2$ is hydrogen, $C_1$-$C_{14}$ linear, branched, or cyclic alkyl, or SR wherein R is glutathione or $R_1$;
wherein the other occurrence of $A_1$ and the other occurrence of $A_2$ is the same or different, and is independently selected from:

i) hydrogen;
ii) —$C_1$-$C_{14}$ linear, branched, or cyclic alkyl optionally substituted with halogen up to perhalo;
iii) —$C_0$-$C_3$ alkyl-phenyl wherein the phenyl moiety is optionally substituted with 1-5 substituents selected from cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, $OCF_3$, $N(R_4)_3X$ wherein X is a counter anion, and wherein the alkyl moiety is optionally substituted with halogen up to perhalo;
vi) —$C_0$-$C_4$-alkyl-K wherein K is a 5- or 6-membered monocyclic heterocyclic ring containing 1-4 atoms selected from O, N, and S or an 8- to 10-membered bicyclic heteroaryl having 1-4 heteroatoms selected from O, N and S, and wherein the alkyl moiety is optionally substituted with halogen up to perhalo;
iv) naphthyl, optionally substituted with 1-5 substituents selected from cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, $OCF_3$, and $N(R_4)_3X$ wherein X is a counter anion;
v) a 5- or 6-membered monocyclic heteroaryl group, having 1-3 heteroatoms selected from O, N, and S, optionally substituted with 1-3 substituents selected from cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, $OCF_3$, and $N(R_4)_3X$ wherein X is a counter anion; or
vi) an 8- to 10-membered bicyclic heteroaryl group containing 1-3 heteroatoms selected from O, N, and S; and the bicyclic hetero aryl group is optionally substituted with 1-3 substituents selected from CN, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, $OCF_3$, and $N(R_4)_3X$ wherein X is a counter anion; and
wherein each $R_4$ and $R_5$ is the same or different and at each occurrence are selected from: hydrogen and $C_1$-$C_{14}$ linear or branched alkyl
wherein each alkyl may be optionally substituted with 1-3 substituents selected from $C_1$-$C_{14}$ linear or branched alkyl, up to perhalo substituted $C_1$-$C_{14}$ linear or branched alkyl, $C_1$-$C_{14}$ alkoxy, nitro, hydroxyl, carboxy, amino, $C_1$-$C_{14}$ alkylamino, $C_1$-$C_{14}$ dialkylamino, halogen, and cyano; and
wherein q is and integer ranging from 0 to 4; or
a geometrical isomer, optical isomer, pharmaceutically acceptable salt, prodrug, or polymorph thereof.

The spirocyclic-guanidine compounds of the invention can also have the structure of formula (Ia),

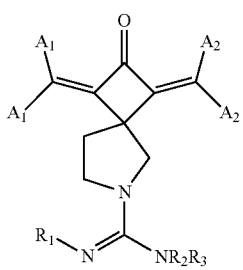

(Ia)

wherein $A_1$, $A_2$, and $R_1$-$R_3$ are as defined above.

The spirocyclic-guanidine compounds of the invention can also have the structure of formula (Ib),

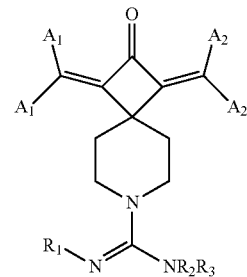

(Ib)

wherein $A_1$, $A_2$, and $R_1$-$R_3$ are as defined above.

The spirocyclic-guanidine compounds of the invention can also have the of formula (Ic),

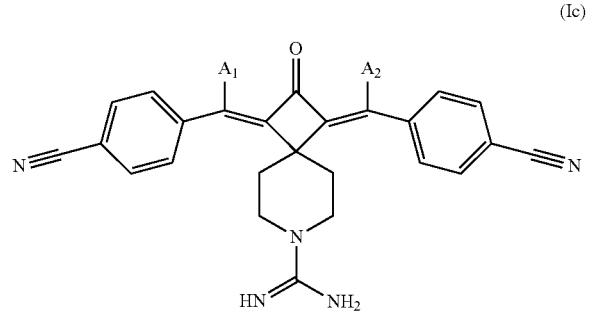

(Ic)

wherein $A_1$ and $A_2$ are independently hydrogen, $C_1$-$C_{14}$ linear, branched, or cyclic alkyl, or SR wherein R is glutathione or $R_1$.

The spirocyclic-guanidine compounds of the invention can also have the structure of formula (Id),

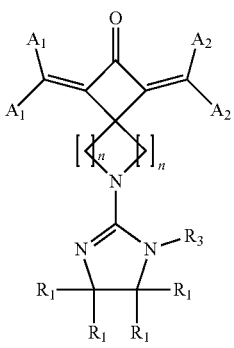

(Id)

wherein $A_1$, $A_2$, n, and $R_1$ and $R_3$ are as defined above.

The spirocyclic-guanidine compounds of the invention can also have the structure of formula (Ie),

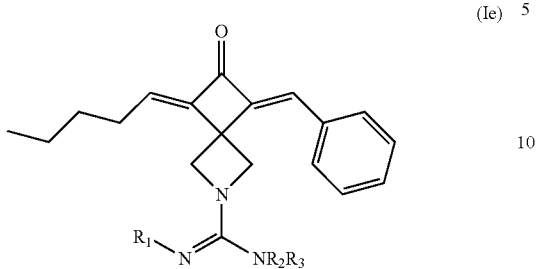 (Ie)

wherein $R_1$-$R_3$ are as defined above.

The spirocyclic-guanidine compounds of formula (I) also includes those compounds wherein least one of $A_1$ or $A_2$ is alkyl selected from:
i) $C_1$-$C_{14}$ linear, branched, or cyclic alkyl optionally substituted with halogen up to perhalo;
ii) $C_0$-$C_3$ alkyl-phenyl, wherein the phenyl moiety is optionally substituted with 1-5 substituents selected from cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, $OCF_3$, and $N(R_4)_3X$ wherein X is a counter anion, and wherein the alkyl moiety is optionally substituted with halogen up to perhalo;
iii) —$C_0$-$C_4$-alkyl-K wherein K is a 5- or 6-membered monocyclic heterocyclic ring containing 1-4 atoms selected from O, N, and S or an 8- to 10-membered bicyclic heteroaryl having 1-4 heteroatoms selected from O, N and S, and wherein the alkyl moiety is optionally substituted with halogen up to perhalo.

The spirocyclic-guanidine compounds of formula (I) also include those compounds wherein one occurrence of $A_1$ and one occurrence of $A_2$ are the same or different and, are independently selected from hydrogen or $C_1$-$C_{14}$ linear, branched, or cyclic alkyl;
wherein the other occurrence of $A_1$ and the other occurrence of $A_2$ are the same or different, and are independently selected from:
i) hydrogen; or
ii) phenyl, optionally substituted with 1-5 substituents selected from CN, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, $OCF_3$, and $N(R_4)_3X$ wherein X is a counter anion;
wherein each $R_4$ and $R_5$ are the same or different and at each occurrence are selected from hydrogen and $C_1$-$C_{14}$ linear or branched alkyl groups.

In certain instances, the other occurrence of A1 and the other occurrence of A2 is the same or different, and is independently selected from 4-cyano phenyl and 3-fluoro-4-cyano phenyl.

The spirocyclic-guanidine compounds of the invention can also have the structure (If),

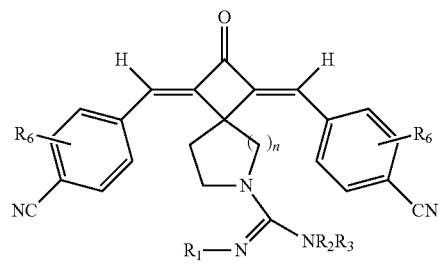

wherein each $R_6$ is independently selected from the group consisting of hydrogen, halogen, CN, $CF_3$, nitro, $C(O)R_4$, $C(O)OR_4$, $S(O)_2R_4$, and $N(R_4)_3X$ wherein X is a counter anion;
and wherein:
i) $R_1$, $R_2$, and $R_3$ are each hydrogen or $R_7$; or
ii) $R_1$ is hydrogen or $R_7$, and $R_2$ and $R_3$, together with the intervening atoms to which they are attached, form a 5- or 6-membered ring, which may include one or more heteroatoms selected from N, O, and S, and may be optionally substituted with one or more $R_7$ groups; or
iii) $R_3$ is H or $R_7$, and $R_1$ and $R_2$, together with the intervening atoms to which they are attached, form a 5- or 6-membered ring, optionally substituted with one or more $R_7$ groups; or
iv) $R_1$ and $R_3$ are H or $R_7$, and $R_2$ is $C(NR_7)NR_7R_7$;
wherein each $R_7$ is the same or different and selected from:
i) —$C_1$-$C_4$ linear, branched, or cyclic alkyl optionally substituted with halogen up to perhalo;
ii) —$C_0$ to $C_3$ alkyl-phenyl wherein the phenyl moiety is optionally substituted with 1-5 substituents selected from cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, and $OCF_3$, and wherein the alkyl moiety is optionally substituted with halogen up to perhalo;
iii) —$C(O)R_4$; and
iv) —$SO_2NR_4R_4$;
and wherein each $R_4$ and $R_5$ are the same or different and are $C_1$-$C_{14}$ linear, branched, or cyclic alkyl, optionally substituted with halogen up to perhalo.

The spirocyclic-guanidine compounds of the invention of formula (If) also include those compounds wherein:
a) $R_6$ is H or 3-fluoro; and
b) $R_1$, $R_2$, and $R_3$ are
  i. each hydrogen;
  ii. $R_1$ is hydrogen and $R_2$ and $R_3$, together with the intervening atoms to which they are attached form a 5- or 6-membered ring, which may include one more heteroatoms selected from N, O and S;
  iii. $R_3$ is H and $R_1$ and $R_2$, together with the intervening atoms to which they are attached form a 5- or 6-membered ring; or
  iv. $R_1$ and $R_3$ are H and $R_2$ is $C(NH)NH_2$.

The invention also includes those compounds of formula (I) wherein n at each occurrence is 2.

The invention also includes those compounds of formula (I) one n is 1 and one n is 2.

The invention also includes those compounds of formula (I) wherein one n is 2 and one n is 3.

The invention also includes those compounds of formula (I) shown below:

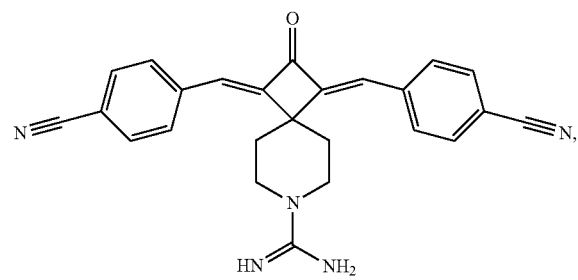

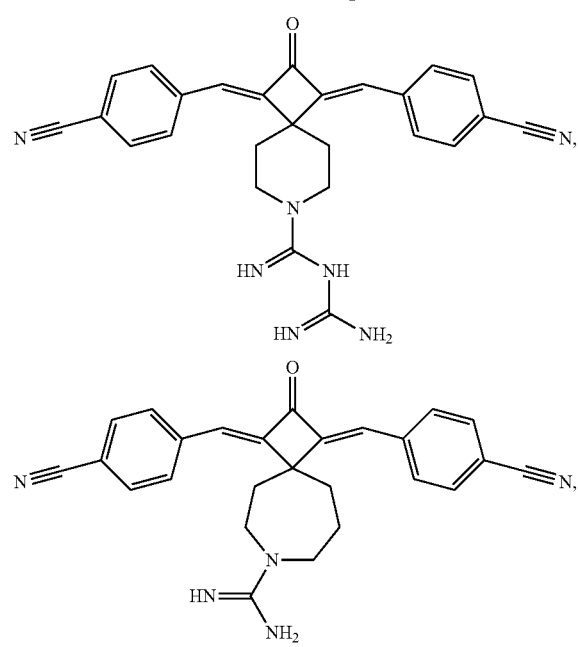

RA477

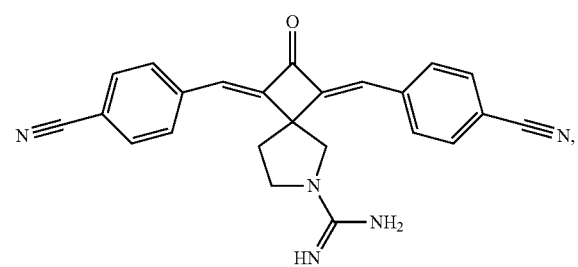

-continued

RA484

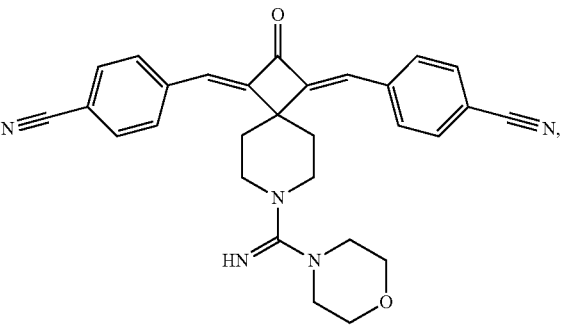

RA479

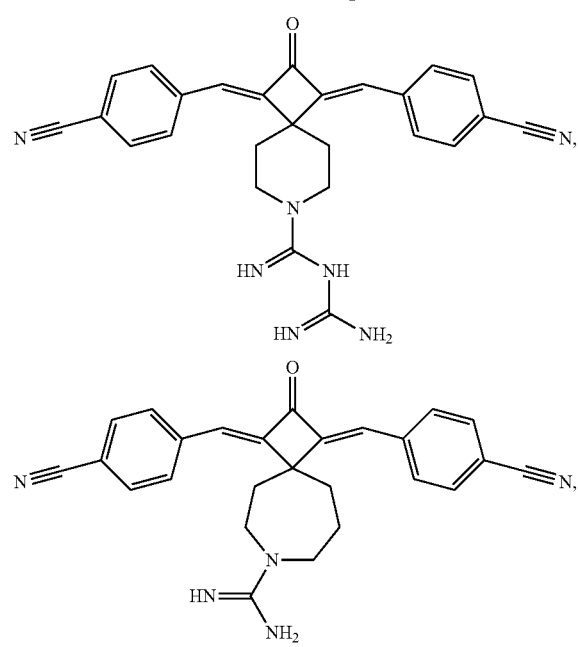

and

RA482

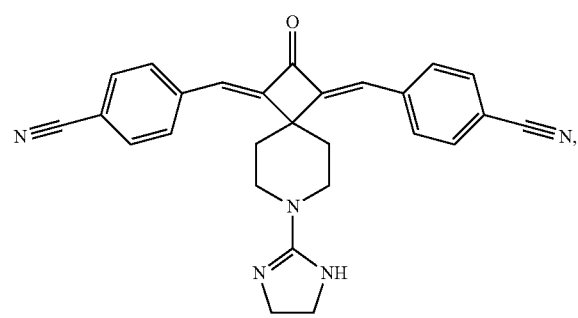

The invention also includes geometrical isomers, optical isomers, pharmaceutically acceptable salts, prodrugs, or polymorphs of the compounds of formula (I). Prodrugs can include, for example folate derivatives and biotin derivatives.

Another aspect of the invention includes methods of treating cancer by administration of an effective amount of a compound of formula (I). In embodiments of the invention, the cancer type can be a solid cancer or a liquid cancer. Types of cancers include, for example, multiple myeloma, ovarian cancer, cervical cancer, breast cancer, liver cancer, and colon cancer.

DESCRIPTION OF THE FIGURES

FIG. 3A shows ES2 cell lysate pretreated with bortezomib or Up compounds (5 μM) and then treated with biotinylated RA190 (RA190B 20 μM). The lysate was separated by SDS-PAGE, transferred to a membrane and probed with HRP-streptavidin. Up compounds, but not bortezomib, compete RA190B binding to the 42 KDa RPN13 (indicated with a star).

FIG. 3B shows ES2 cell lysate treated with RA190B and biotinylated Up284 (Up284B) at indicated concentrations and probed for HRP-Streptavidin.

FIG. 7A shows ES2 cells stably expressing 4UbFL with a dose-dependent increase in bioluminescence after 4 hr treatment with Up284 and RA475 as measured by a luminometer. Data are presented as fold increase over bioluminescence of cells treated with vehicle alone (DMSO).

FIG. 7B shows CD-1 mice electroporated after injection of 4UbFL plasmid into the muscle of one leg and tagged. Administration of luciferin substrate i.p. and IVIS200 imaging of the mice at the site of 4UbFL plasmid injection was performed 24 hr after electroporation. This time point was considered baseline. Mice were then randomized into three groups (n=5) and treated with vehicle alone (25% β-hydroxypropylcyclodextrin-water solution), RA475 (40 mg/Kg) and Up284 (40 mg/Kg) administered as a single i.p. dose. The mice were imaged again at 4 hr, 24 hr, 48 hr, 72 hr and 96 hr later. Data are presented as fold increase over bioluminescence of injection site at baseline for individual mice followed longitudinally.

FIG. 10A shows RA475 controlled tumor growth compared to vehicle alone.

FIG. 10B shows the survival of mice treated with RA475 compared to vehicle alone.

FIG. 10C shows no weight loss was observed in mice treated with RA475.

DETAILED DESCRIPTION OF THE INVENTION

Figure 1:
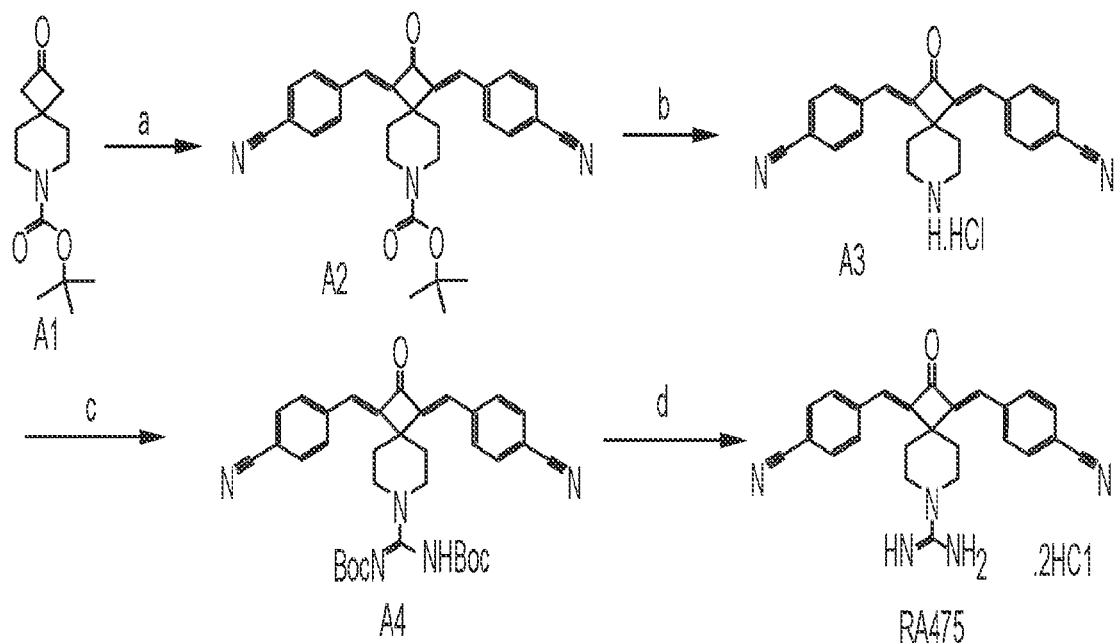
FIG. 1 shows the synthesis route of compound RA475.

The following description is provided to enable any person skilled in the art to make and use the invention. Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. Various modifications, however, will remain readily apparent to those skilled in the art, since the general principles of the present invention have been defined herein specifically to provide one example of one application of the invention. All references cited herein are incorporated by reference as if each had been individually incorporated.

The spirocyclic-guanidine compounds of the invention have the general structure of formula (I) shown below:

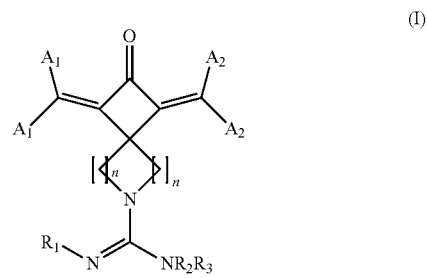

(I)

wherein at each occurrence n is an integer independently selected from 1-3;

wherein $R_2$ is $C(NR_1)NR_3R_3$, $R_1$, or $R_3$; or wherein $R_1$ and $R_3$ together with the intervening atoms to which they are attached form a 5- or 6-membered heterocycle optionally substituted with one or more $R_1$ groups; or wherein $R_2$ and $R_3$ together with the intervening atoms to which they are attached form a 5- or 6-membered heterocycle optionally substituted with one or more $R_1$ groups;

wherein each $R_1$ and $R_3$ may be the same or different and are selected from the group consisting of:

i) hydrogen;

ii) —$C_1$-$C_{14}$ linear, branched, or cyclic alkyl optionally substituted with halogen up to perhalo;

iii) —$C_0$-$C_3$ alkyl-phenyl wherein the phenyl moiety is optionally substituted with 1-5 substituents selected from the group consisting of cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, and $OCF_3$, and wherein the alkyl moiety is optionally substituted with halogen up to perhalo;

iv) —$C_0$-$C_4$-alkyl-K wherein K is a 5- or 6-membered monocyclic heterocyclic ring containing 1-4 atoms selected from O, N, and S or an 8- to 10-membered bicyclic heteroaryl having 1-4 heteroatoms selected from the group consisting of O, N and S, and wherein said alkyl moiety is optionally substituted with halogen up to perhalo;

v) —$C(O)R_4$; and vi) —$SO_2NR_4R_4$; and wherein one occurrence of $A_1$ and one occurrence of $A_2$ is hydrogen, $C_1$-$C_{14}$ linear, branched, or cyclic alkyl, or SR wherein R is glutathione or $R_1$;

wherein the other occurrence of $A_1$ and $A_2$ is the same or different, and is independently selected from the group consisting of:

i) hydrogen;

ii) —$C_1$-$C_{14}$ linear, branched, or cyclic alkyl optionally substituted with halogen up to perhalo;

iii) —$C_0$-$C_3$ alkyl-phenyl wherein the phenyl moiety is optionally substituted with 1-5 substituents selected from the group consisting of cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, $OCF_3$, and $N(R_4)_3X$ wherein X is a counter anion, and wherein the alkyl moiety is optionally substituted with halogen up to perhalo;

iv) —$C_0$-$C_4$-alkyl-K wherein K is a 5- or 6-membered monocyclic heterocyclic ring containing 1-4 atoms selected from O, N, and S or an 8- to 10-membered bicyclic heteroaryl having 1-4 heteroatoms selected from the group consisting of O, N and S, and wherein the alkyl moiety is optionally substituted with halogen up to perhalo;

v) naphthyl, optionally substituted with 1-5 substituents selected from the group consisting of cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, $OCF_3$, and $N(R_4)_3X$ wherein X is a counter anion;

vi) a 5- or 6-membered monocyclic heteroaryl group, having 1-3 heteroatoms selected from the group consisting of O, N, and S, optionally substituted with 1-3 substituents selected from the group consisting of cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, $OCF_3$, and $N(R_4)_3X$ wherein X is a counter anion; or vii) an 8- to 10-membered bicyclic heteroaryl group containing 1-3 heteroatoms selected from the group consisting of O, N, and S; and the bicyclic hetero aryl group is optionally substituted with 1-3 substituents selected from the group consisting of CN, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, $OCF_3$, and $N(R_4)_3X$ wherein X is a counter anion; and wherein $R_4$ and $R_5$ at each occurrence are selected from the group consisting of:
hydrogen and $C_1$-$C_{14}$ linear or branched alkyl, wherein each alkyl may be optionally substituted with 1-3 substituents selected from the group consisting of $C_1$-$C_{14}$ linear or branched alkyl, up to perhalo substituted $C_1$-$C_{14}$ linear or branched alkyl, $C_1$-$C_{14}$ alkoxy, nitro, hydroxyl, carboxy, amino, $C_1$-$C_{14}$ alkylamino, $C_1$-$C_{14}$ dialkylamino, halogen, and cyano; and
wherein q is and integer ranging from 0 to 4.

In embodiments, the compound of formula (I) can be a geometrical isomer, optical isomer, pharmaceutically acceptable salt, prodrug, or polymorph thereof. In embodiments the product can be a folate derivative or a biotin derivative.

In one embodiment at least one of $A_1$ or $A_2$ can be an alkyl group, such as:
—$C_1$-$C_{14}$ linear, branched, or cyclic alkyl optionally substituted with halogen up to perhalo;
—$C_0$-$C_3$ alkyl-phenyl, wherein the alkyl moiety is optionally substituted with 1-5 substituents selected from the group consisting of cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, and $OCF_3$, and wherein the alkyl moiety is optionally substituted with halogen up to perhalo; or —$C_0$-$C_4$-alkyl-K wherein K is a 5- or 6-membered monocyclic heterocyclic ring containing 1-4 atoms selected from O, N, and S or an 8- to 10-membered bicyclic heteroaryl having 1-4 heteroatoms selected from the group consisting of O, N and S, and wherein the alkyl moiety is optionally substituted with halogen up to perhalo.

In another embodiment, one occurrence of $A_1$ and one occurrence of $A_2$ are the same or different and are independently hydrogen or $C_1$-$C_{14}$ linear, branched, or cyclic alkyl;
wherein the other occurrence of $A_1$ and the other occurrence of $A_2$ are the same or different, and is independently selected from the group consisting of:
i) hydrogen; or
ii) phenyl, optionally substituted with 1-5 substituents selected from the group consisting of CN, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, and $OCF_3$;
wherein $R_4$ and $R_5$ are the same or different and at each occurrence are selected from the group consisting of hydrogen and $C_1$-$C_{14}$ linear or branched alkyl groups.

In another embodiment, the other occurrence of A1 and the other occurrence of A2 are the same or different, and are independently selected from the group consisting of 4-cyano phenyl and 3-fluoro-4-cyano phenyl.

In an embodiment of the invention, n at each occurrence is 2. In another embodiment one n is 1 and the other n is 2. In another embodiment one n is 2 and the other n is 3.

In exemplary embodiments, one A1 is methyl and one A2 is methyl, such that the compounds have the structure shown below:

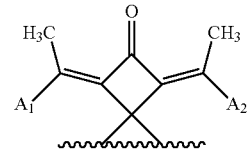

wherein $A_1$ and $A_2$ are not H.

In other exemplary embodiments, one A1 is hydrogen and one A2 is hydrogen, such that the compounds have the structure shown below:

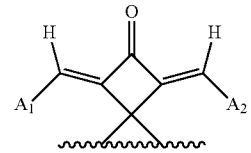

wherein $A_1$ and $A_2$ are not H.

The invention also encompasses compounds of the general formulas shown below:

A structure of formula (Ia),

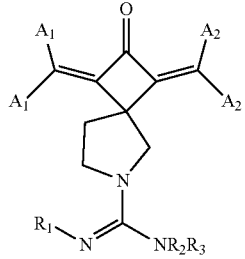

(Ia)

wherein $A_1$, $A_2$, and $R_1$-$R_3$ are as defined above.

A structure of formula (Ib),

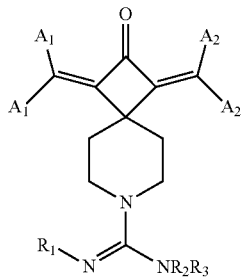

(Ib)

wherein $A_1$, $A_2$, and $R_1$-$R_3$ are as defined above.

A structure of formula (Ic),

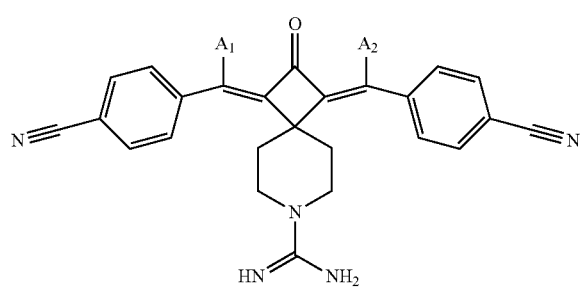

(Ic)

wherein $A_1$ and $A_2$ are independently hydrogen, $C_1$ to $C_{14}$ linear, branched, or cyclic alkyl, or SR wherein R is glutathione or $R_1$.

A structure of formula (Id),

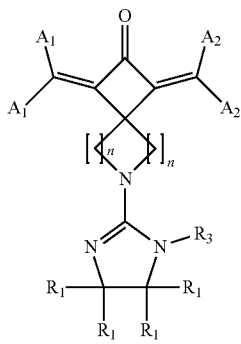

(Id)

wherein $A_1$, $A_2$, n, and $R_1$ and $R_3$ are as defined above.

A structure of formula (Ie), (Ie)

wherein $R_1$-$R_3$ are as defined above.

A structure of formula (If),

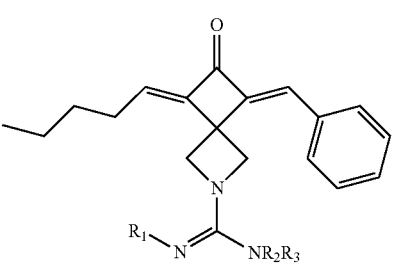

(If)

wherein each $R_6$ is independently selected from hydrogen or an electron withdrawing group such as halogen, CN, $CF_3$, nitro, $C(O)R_4$, $C(O)OR_4$, $S(O)_2R_4$, and $N(R_4)_3X$ wherein X is a counter anion, such as halogen (particularly chlorine, bromine, or iodine), carbonate or bicarbonate, sulphate or bisulphate, phosphate or hydrogen phosphate or dihydrogen phosphate and the like;

and wherein:
  i) $R_1$, $R_2$, and $R_3$ are each hydrogen or $R_7$; or
  ii) $R_1$ is hydrogen or $R_7$, and $R_2$ and $R_3$, together with the intervening atoms to which they are attached, form a 5- or 6-membered ring, which may include one or more heteroatoms selected from N, O, and S, and may be optionally substituted with one or more $R_7$ groups; or
  iii) $R_3$ is H or $R_7$, and $R_1$ and $R_2$, together with the intervening atoms to which they are attached, form a 5- or 6-membered ring, optionally substituted with one or more $R_7$ groups; or iv) $R_1$ and $R_3$ are H or $R_7$, and $R_2$ is $C(NR_7)NR_7R_7$;

wherein each $R_7$ is the same or different and selected from the group consisting of:

v) —$C_1$-$C_{14}$ linear, branched, or cyclic alkyl optionally substituted with halogen up to perhalo;

vi) —$C_0$ to $C_3$ alkyl-phenyl wherein the phenyl moiety is optionally substituted with 1-5 substituents selected from the group consisting of cyano, halogen, nitro, $R_4$, $OR_4$, $NR_4R_5$, $S(O)_qR_4$, $SO_2NR_4R_5$, $NR_4SO_2R_5$, $C(O)R_4$, $C(O)OR_4$, $C(O)NR_4R_5$, $NR_4C(O)R_5$, $NR_4C(O)OR_5$, $CF_3$, and $OCF_3$, and wherein the alkyl moiety is optionally substituted with halogen up to perhalo;

vii) —$C(O)R_4$; and viii) —$SO_2NR_4R_4$;

and wherein $R_4$ and $R_5$ are the same or different and are $C_1$-$C_{14}$ linear, branched, or cyclic alkyl, optionally substituted with halogen up to perhalo.

In a preferred embodiment of compound (If), a) $R_6$ is H or 3-fluoro; and b) $R_1$, $R_2$, and $R_3$ are i) each hydrogen;

ii) $R_1$ is hydrogen and $R_2$ and $R_3$, together with the intervening atoms to which they are attached form a 5- or 6-membered ring, which may include one more heteroatoms selected from N, O and S;

iii) $R_3$ is H and $R_1$ and $R_2$, together with the intervening atoms to which they are attached form a 5- or 6-membered ring; or iv) $R_1$ and $R_3$ are H and $R_2$ is $C(NH)NH_2$.

Exemplary compounds include, but are not limited to, the following,

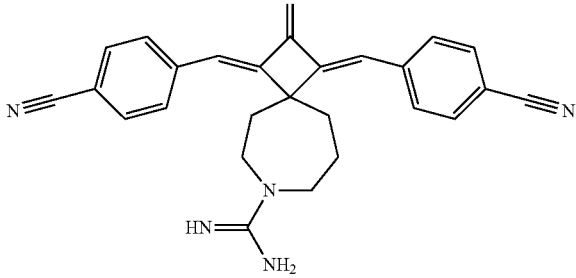

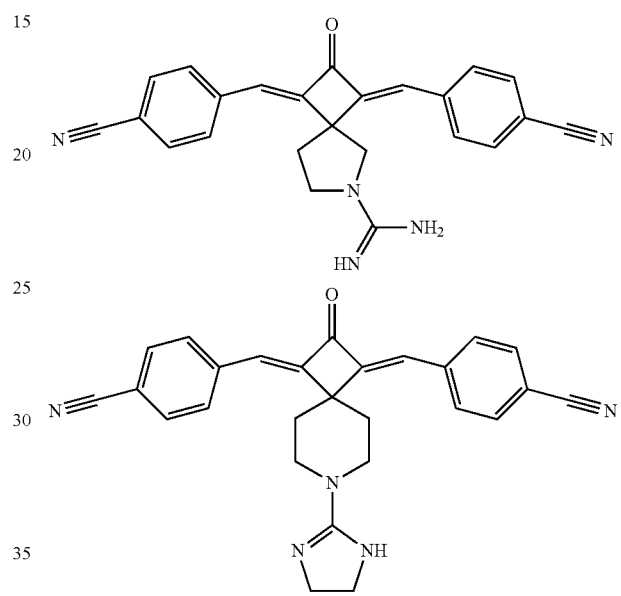

RA477

RA484

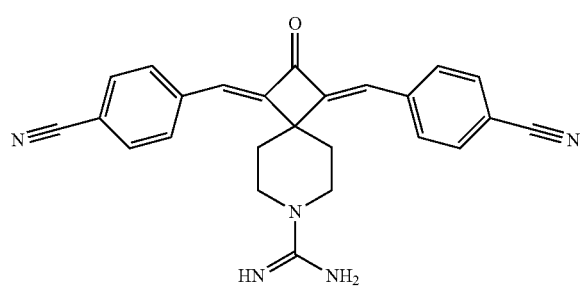

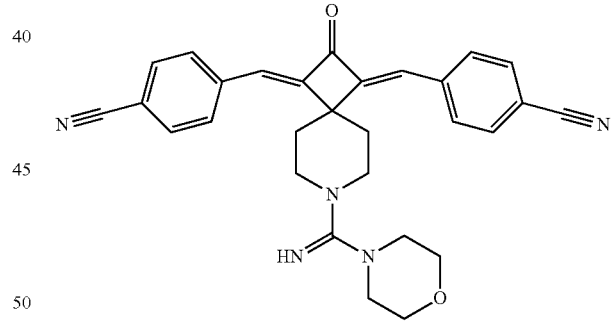

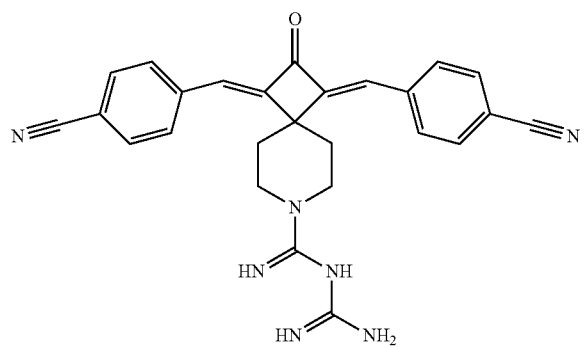

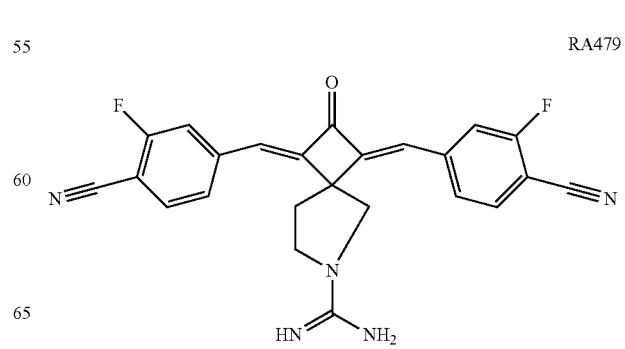

RA479

-continued

RA482

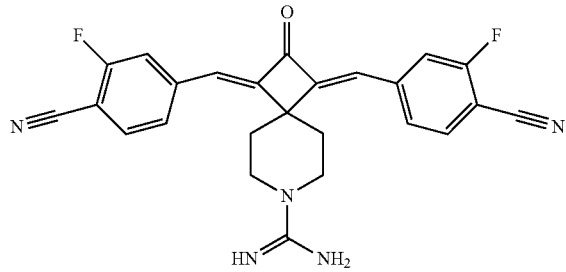

RA475 was synthesized as described in FIG. 1. Chemical probes for RPN13, either biotinylated RA190 (i.e., RA190B) synthesized as described previously (34), or biotinylated Up284B were provided by Up Therapeutics LLC, (Elkridge, MD), along with other Up-compounds such as Up284 (FIG. 2), Up104, Up109, Up111, and Up285, that are described in WO 2018/140907A1.

The invention also includes geometrical isomers, optical isomers, pharmaceutically acceptable salts, prodrugs, or polymorphs of the compounds of formula (I).

Prodrugs include, for example, folic acid or biotin derivatives of the compounds of formula (I), formed by replacing one or more of the guanidine hydrogens.

Targeted delivery of high doses of chemotherapeutics using ligands is important for cancer cell death, and may be an attractive alternative approach for the successful treatment of cancer. Such important ligands investigated for targeted drug delivery in recent years are folic acid and biotin.

Many cancer cells have a high requirement for folic acid and overexpress the folic acid receptor. This finding has led to the development of anti-cancer drugs that target the folic acid receptor. Folate is important for cells and tissues that rapidly divide. Cancer cells divide rapidly, and drugs that interfere with folate metabolism are used to treat cancer. The anti-folate methotrexate is a drug often used to treat cancer because it inhibits the production of the active tetrahydrofolate (THF), which is required to synthesize nucleic acids, from the inactive dihydrofolate (DHF). However, methotrexate can be toxic, producing side effects, such as inflammation in the digestive tract that make it difficult to eat normally.

Biotin is essential for cell growth, the production of fatty acids, the metabolism of fats and amino acids, and growth and development. Humans cannot synthesize biotin and it is generally supplemented from exogenous dietary sources and from intestinal bacteria. The high metabolisms of cancer cells make them depend on vitamins such as biotin (vitamin B7). Biotin levels were found to be significantly higher in many cancers, especially colon and ovarian cancer tissues, compared to normal tissue. At the same time, these tumor cells over express biotin receptors along with folate receptors. Several research groups are pursuing biotinylated prodrugs that target biotin receptors. For example, biotinylated conjugates of camptothecin have been shown to be more cytotoxic and induce apoptosis by activation of the caspase-dependent cell death signaling pathway and were effective against multidrug resistant ovarian carcinoma cells. High availability and flexible syntheses makes biotinylated prodrugs open up a new avenue in targeted drug delivery for overcoming resistance to chemotherapy.

Accordingly, biotin and folate versions of the inventive molecules are encompassed by the instant disclosure.

Figure 3:
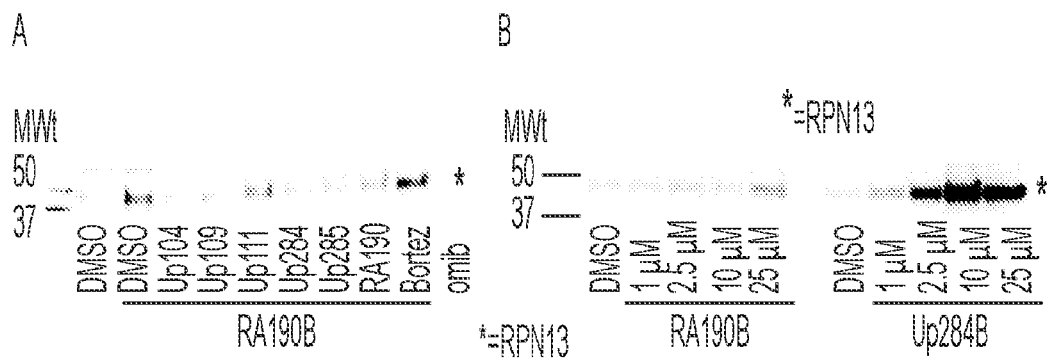
FIG. 3 shows Up284 binds to RPN13 much more strongly than RA190B.
Figure 5:
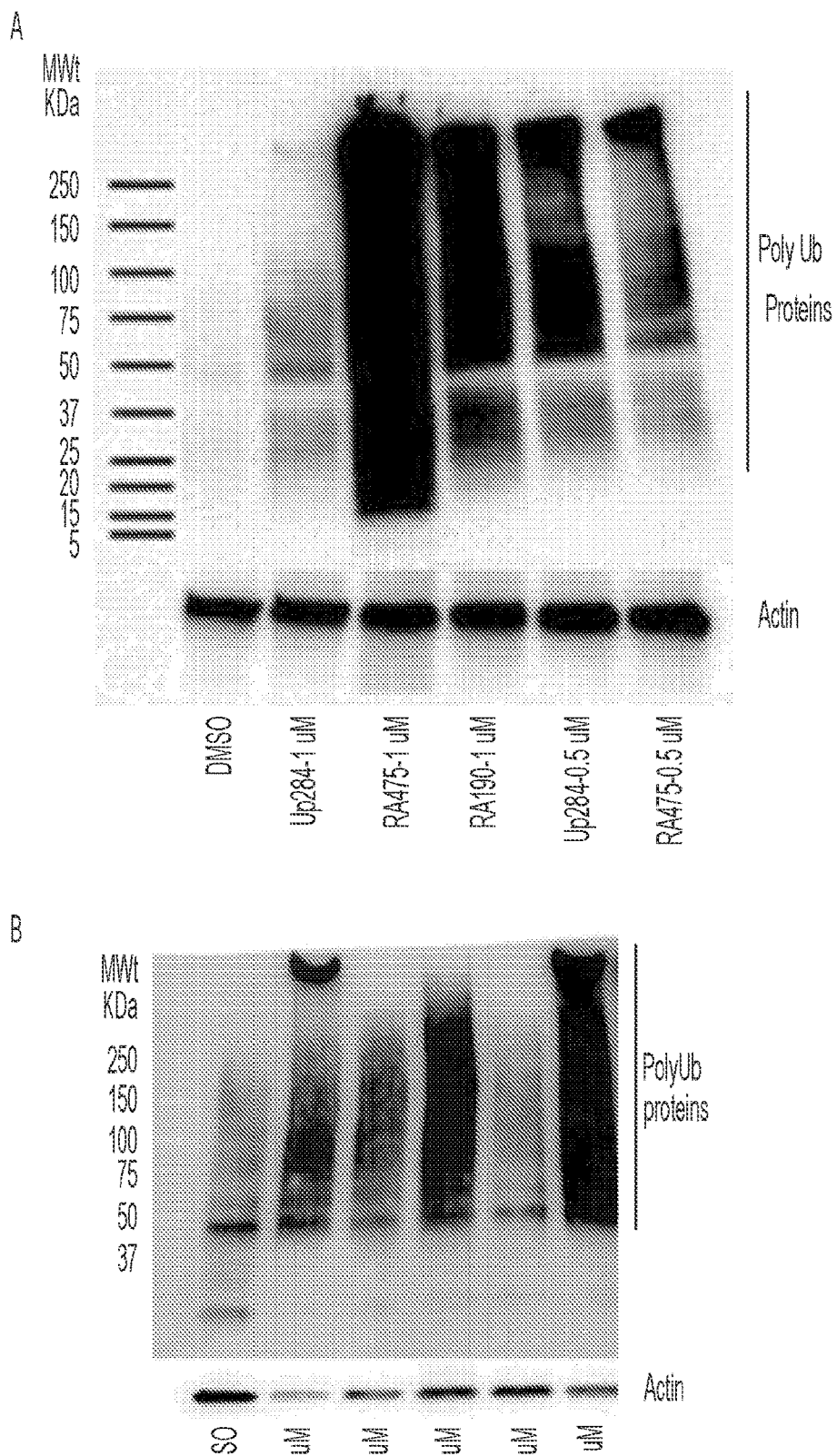
FIG. 5A shows RA475 triggers the accumulation of high molecular weight polyubiquitinated proteins in SKOV3 cells treated with Up284 (0.5 µM and 1 µM), 1 µM RA190, RA475 (0.5 µM and 1 µM) or vehicle alone (DMSO).
FIG. 5B shows RA475 triggers the accumulation of high molecular weight polyubiquitinated proteins in OVCAR3 cells treated with Up284 (0.5 µM), Bz (0.25 µM), Iz (0.25 µM), RA475 (0.5 µM and 1 µM), or vehicle alone (DMSO).
Figure 6:
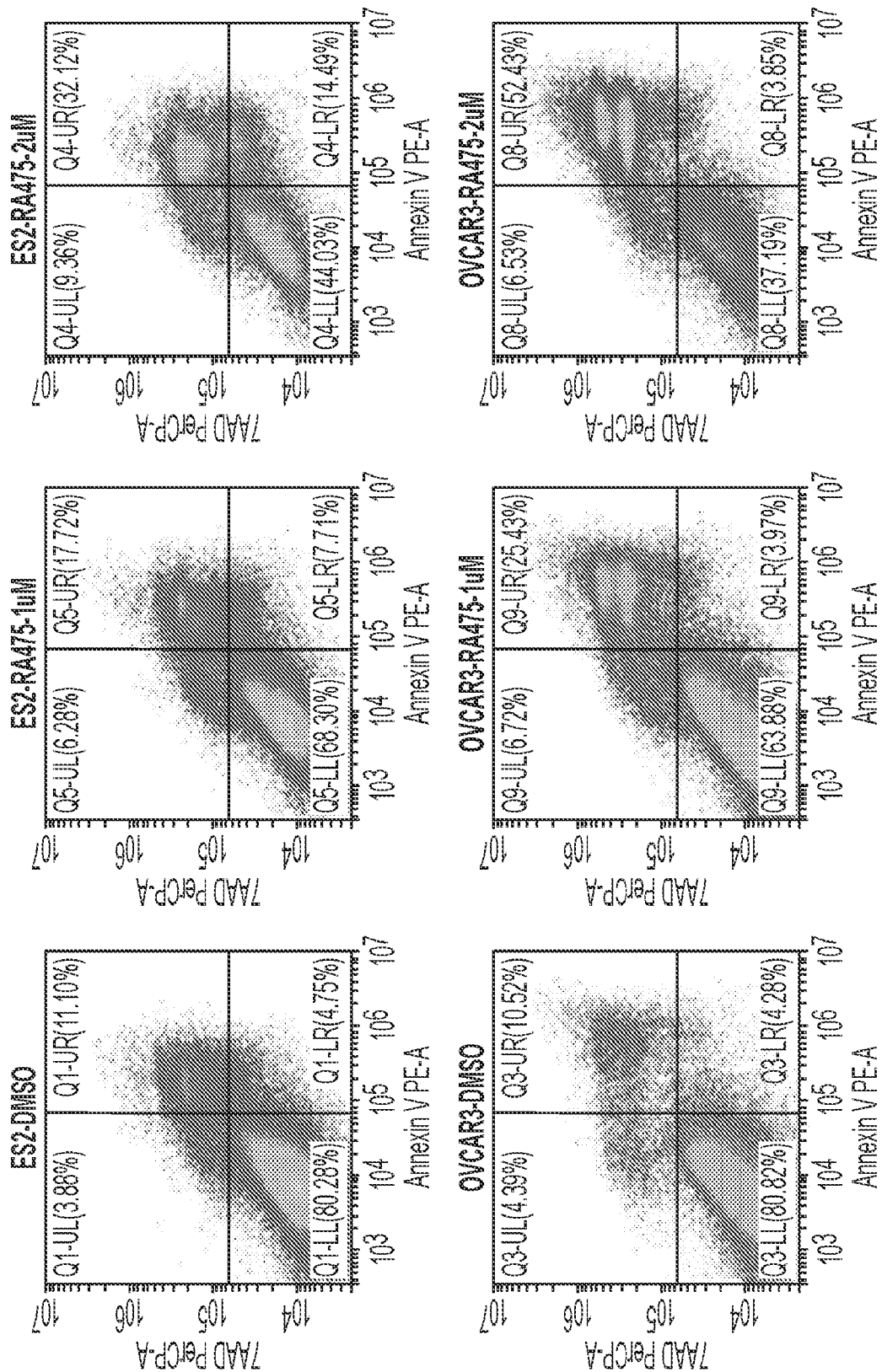
FIG. 6 shows RA475 induces apoptosis in ovarian cancer cells.
Figure 7:
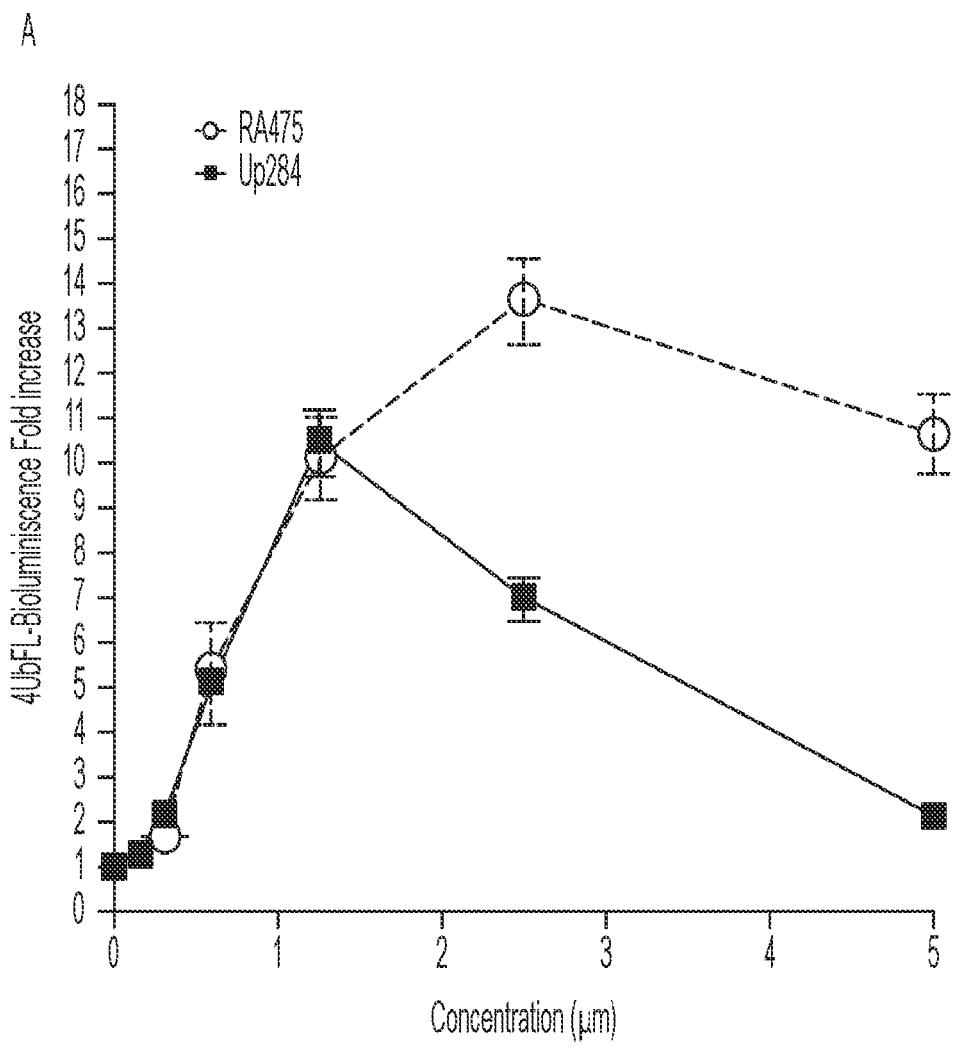
FIG. 7 shows on-target activity of Up284 and RA475 in cells and mice.
Figure 7:
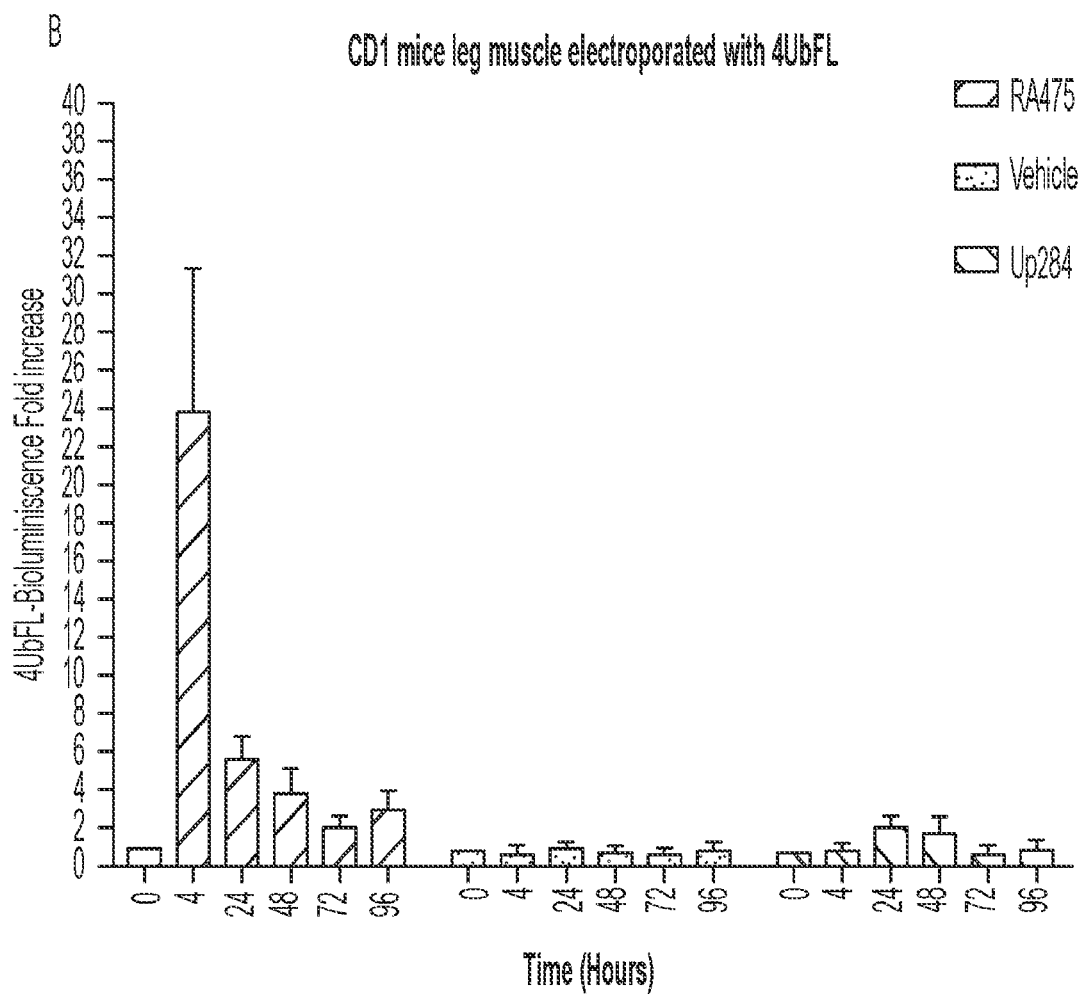

RA475 addresses many limitations associated with the prototypic RPN13 inhibitor RA190 in terms of (i) better solubility, (ii) longer liver microsomal and plasma stability, (iii) stronger on-target activity, (iv) lack of PAINS structural moiety (49), and (v) limited brain access based upon Swiss ADME analysis. Through its covalent binding to the 42 kDa cellular protein identified as the 19S RP ubiquitin receptor RPN13 (FIG. 3-4), RA475 exhibits cytotoxic activity against cell lines derived from a variety of solid malignancies, including ovarian, breast, cervical, liver and colon cancer (Table 1) that is associated with inhibition of proteasome function (FIG. 7), accumulation of proteotoxic stress (FIGS. 5A and 5B) and apoptosis (FIG. 6). RA475 shows a significant therapeutic window between normal human fibroblasts (IC50>2.5 µM) and cancer cells (IC50 0.1 µM-0.75 µM, Table 1). Importantly, RA475 was well tolerated by CD-1 mice (NOAEL>80 mg/kg for a single dose) and showed on-target activity in vivo. Interestingly, when RA475 was administered i.p. it rapidly and profoundly inhibited proteasome function in the leg muscle, suggesting rapid and sustained entry to the circulation, whereas this was slower and much weaker for Up284 (FIG. 7). Since both drugs are stable in plasma (Tables 2 and 4), this difference may reflect the greater stability of RA475 than Up284 in liver microsomes (Tables 3 and 5). One concludes that RA475 is a more drug-like than the prototypic iRPN13 RA190, and that novel spirocyclic-guanidine compounds including RA475 have potential as treatments for both liquid and solid cancers.

Methods

Another aspect of the invention includes methods of treating cancer by administration of an effective amount of a compound of formula (I). Examples of cancers to be treated include, for example, multiple myeloma, ovarian cancer, cervical cancer, breast cancer, liver cancer, or colon cancer. The cancer can be a liquid cancer or a solid cancer Synthesis of Compound RA475

Commercially available A1 (1 mmol) was dissolved in ethanol (20 mL) and 30% NaOH solution was added drop wise at 0° C. Next, corresponding benzaldehyde (2 mmol) was added to the solution. Stirring continued for 30 min at room temperature and ethanol was removed under reduced pressure and the crude was extracted with water and ethyl acetate. Ethyl acetate layer was collected and dried over sodium sulfate and concentrated under vacuum. The crude compound was purified by column chromatography using hexanes and ethyl acetate to afford compound A2.

Compound A2 was added to 4M HCl in dioxane and stirred at room temperature for 30 min. Diethyl ether was added and the yellow precipitate was collected and washed several times with diethyl ether and hexanes. Compound A3 was dried and collected.

Compound A3 (1 mmol) was dissolved in acetonitrile (20 mL) and triethyl amine (6 mmol) and N,N-bis-boc-1-guanylpyrazole (1.1 mmol) was added subsequently and refluxed overnight. Solvents were removed under reduced pressure and the crude was purified by column chromatography using hexanes and ethyl acetate as solvents to afford compound A4.

Compound A4 was dissolved in 4M HCl in dioxane and stirred at room temperature for 30 min. Diethyl ether was added and the yellow precipitate was collected and washed several times with diethyl ether and hexanes. Compound RA475 was dried and collected. MS: m/z: 408 (M+1).

The resulting RA475 had a purity of >97% as confirmed by NMR and MS.

Cell Lines and Cytotoxicity Assays

All cell lines were obtained from the American Type Culture Collection (ATCC) and cultured in the specified medium supplemented with 10% fetal bovine serum, 100 IU/mL penicillin, and 100 µg/mL streptomycin at 37° C. in a humidified 5% $CO_2$/95% air incubator. To assess drug cytotoxicity cells were seeded at 2,500 cells/well (10,000 cells/well for MM lines and primary cells) in 100 µL medium in 96-well plate. The cells were treated with compounds for 48 h, and cells were incubated according to the manufacturer's protocol with the Thiazolyl Blue Tetrazolium Bromide (Sigma, M2128) and $A_{570}$ measured using a Benchmark Plus microplate spectrophotometer (BIO-RAD).

Antibodies and Western Blot Analyses

Cell lysate (10-20 µg total protein) prepared in MPER (Pierce) from each sample was subjected to SDS-PAGE, transferred to PVDF membranes and analyzed by Western blot using antibodies specific for ubiquitin (P4D1, sc-8017, Santa Cruz), or after stripping antibody for actin (#66009, Protein Tech Group), at the dilutions recommended by the manufacturers, and for secondary antibodies either peroxidase-linked anti-mouse IgG or anti-rabbit IgG (GE Healthcare UK Ltd) were utilized at the recommended dilution. The blots were developed using HyGLO chemiluminescent detection reagent (Denville).

Flow Cytometry Analysis of Cell Death $10^5$ cells were re-suspended in binding buffer, 5 µL of Annexin V-PE (Apoptosis Detection Kit I (BD Pharmingen) and 5 µL of 7-AAD were then added into the cells, which were then incubated at room temperature for 15 minutes and analyzed by flow cytometry on a FACSCalibur using CellQuest software (Becton Dickinson).

RA190B and Up284B Competitive Labeling Assay

Clarified cell lysate (40 ug/sample) in MPER buffer was pretreated with streptavidin-coated magnetic beads for 45 min at 4° C. to deplete non-specific biotinylated proteins in the cell lysate. The beads were separated and 40 µL of the pre-cleared cell lysate was incubated with compounds (20 µM) for 45 min at 4° C., and then treated with RA190B (20 µM) or Up284B (5 µM) for 45 min at 4° C. Next, the samples were mixed with Laemmli sample buffer (BioRad) and boiled for 5 min. The proteins were separated using a 4-15% Bio-Rad Mini-PROTEAN SDS-PAGE gel (1 hr at 100 V), and transferred to PVDF membrane overnight at 4° C. (24 V). The membrane was blocked with 5% BSA in PBST for 1 hr at RT and washed for 20 minutes (3× with PBST). Then the membrane was probed with HRP-streptavidin (1:10,000 in PBST) for 1 hr at RT, washed for 30 min (3× with PBST), and developed using HyGLO chemiluminescent detection reagent (Denville) for biotin detection.

In Vitro 4UbFL Assay

Sub-confluent cultures of ES2 cells stably expressing 4UbFL were seeded at 10,000 cells/well in 96-well microtiter plates. At 18 hr post transfection, cells were treated with compounds or vehicle (DMSO) at the doses indicated. After a 4 hr incubation, the cells were lysed and the luciferase activity in each cell lysate was determined with a luciferase assay kit (Promega) according to the manufacturer's instructions. Bioluminescence was measured by using a luminometer (Glomax Multidetection system, Promega).

Microsomal, Plasma and Neat Solution Stability

Human and mouse liver microsomes and NADPH regenerating system solutions were purchased from Corning Life Sciences (Tewsbury, MA). Human and mouse K2EDTA was purchased from BioIVT (Westbury, NY). Metabolic studies in liver microsomes (0.125 mg/mL) were conducted in 1× phosphate buffered saline (pH 7.4), NADPH-generating system, and 10 µM of RA475 in a final volume of 250 µl. An incubation mixture with and without NADPH-generating system as well as a neat solution without microsomes and NADPH-generating system were prepared. RA475 was added at the same concentration level into human and mouse EDTA plasma. All reactions were initiated with the addition of RA475. Incubations were performed in glass tubes maintained at 37° C. in a shaker bath. At 0, 30, and 60 minutes, 10 µL aliquots were sampled from the reaction mixture and 0.5 mL of acetonitrile containing internal standard (Up284) was added to each samples. Samples were vortex-mixed and underwent centrifugation for 5 min at 1430×g. A 10 µL aliquot of the supernatant was injected onto the LC-MS instrument for qualitative analysis using a temperature-controlled autosampling device operating at 5° C. Chromatographic analysis was performed using a Waters Acquity™ Ultra Performance LC. Separation of the analyte from potentially interfering material and metabolites was achieved at ambient temperature using a Agilent Zorbax XDB C18 column (3.5 µm, 50×2.1 mm i.d.; Santa Clara, CA). The mobile phase used for the chromatographic separation was composed of water (mobile phase A) and acetonitrile (mobile phase B) containing 0.1% (v/v) formic acid with a flow rate of 0.3 mL/min. The initial mobile phase composition was 80% mobile phase A and 20% mobile phase B. From 0.5 to 1 min, mobile phase B was increased linearly from 20% to 100%. From 1 to 3 min, mobile phase B was maintained at 100%. From 3.0 to 3.1 min, the gradient decreased to 20% mobile phase B and the conditions were maintained until 4.1 min to re-equilibrate the column for the next injection. The column effluent was monitored using an AB Sciex 5500 triple quadrupole mass spectrometer. The instrument was equipped with an electrospray interface, operated in a positive mode and controlled by the Analyst v1.6 software. For the stability study, the mass spectrometer was programmed to monitor the following MRM transition 408.2→366.1 for RA475 and 366.2→155.8 for UP284 (internal standard). Results were assessed qualitatively comparing the average area ratio of RA475 at 0 hr to area ratio at 30 and 60 minutes for both mouse and human liver microsomes. RA475 was not analyzed for metabolites due to the concentration of RA475 not decreasing.

Animal Studies

All animal procedures were performed according to protocols approved by the Johns Hopkins University Animal Care and Use Committee, and in accordance with the AAALAC recommendations for the proper use and care of laboratory animals (protocol MO15M375, renewed as MO18M129). Four to six week old female CD-1 mice were purchased from Jackson Laboratories (ME, USA). Isoflurane anesthesia was used during imaging. The health conditions and/or criteria under which early euthanasia or withdrawal of an animal from the study was implemented included, but are not limited to, general signs of distress such as hunched posture, lethargy, anorexia, dehydration, rough hair coat and/or those that are directly related to the experimental procedures e.g. loss of weight >10%, lethargy, restricted movement of limbs, distended abdomen. Animals in distress were euthanized by carbon dioxide asphyxiation, and cervical dislocation was used to ensure death. This is an acceptable form of euthanasia for mice and in compliance with the recommendations of the Panel on Euthanasia of the American Veterinary Medical Association.

Measurement of On-Target Activity In Vivo Using 4UbFL

A patch was shaved of hair on one leg of CD-1 mice, and 10 μg 4UbFL plasmid in 20 μL of PBS was injected into the quadriceps femoralis muscle followed immediately by injection of the 2 Needle Array to 5 mm depth encompassing the injection site and square wave electroporation (ElectroSquarePorator 833, BTX-2 Needle array 5 mm gap, Harvard apparatus) delivered as eight pulses at 106V for 20 ms with 200 ms intervals. One day post electroporation, mice were anesthetized with isoflurane, injected i.p. with luciferin (0.3 mg in 100 μL water) and optical imaging was performed to determine basal level luciferase expression. Images were acquired for 10 min with a Xenogen IVIS 200 (Caliper, Hopkinton, MA). Equally sized areas were analyzed using Living Image 2.20 software. Mice were imaged weekly during treatment. Mice were randomized into three groups (n=5) and treated i.p. once with Vehicle (25% (w/v) β-Hydroxypropylcyclodextrin in water, Sigma Aldrich), RA475 (40 mg/Kg) and Up284 (40 mg/Kg) and mice were imaged again at 4 hr, 24 hr, 48 hr, 72 hr and 96 hr later.

Statistical Analysis

Results are reported as mean±standard deviation (s.d.). Statistical significance of differences was assessed by ordinary 1-way ANOVA using Tukey's multiple comparison test in Prism (V.8.2.0 Graphpad, San Diego, CA) to correct for the false discovery rate with the level of significance set at p≤0.05.

Results

The iRPN13 RA475 (FIG. 1) is a bicyclic spiro-bis-benzylidine-guanidine piperidone derivative, and thus differs from prior iRPN13 candidates (such as, for example, RA183, RA190 and RA375, shown below), as well as the Up-series compounds (16). RA475 is identified by in silico screening for a PAINS core structural moiety using SWISS-ADME (47) and badapple software (48). Likewise, based on in silico analysis of its chemical structure, RA475 possess drug-like characteristics described by Lipinski, Ghose, Veber, Egan and Muegge rules (Swiss ADME software).

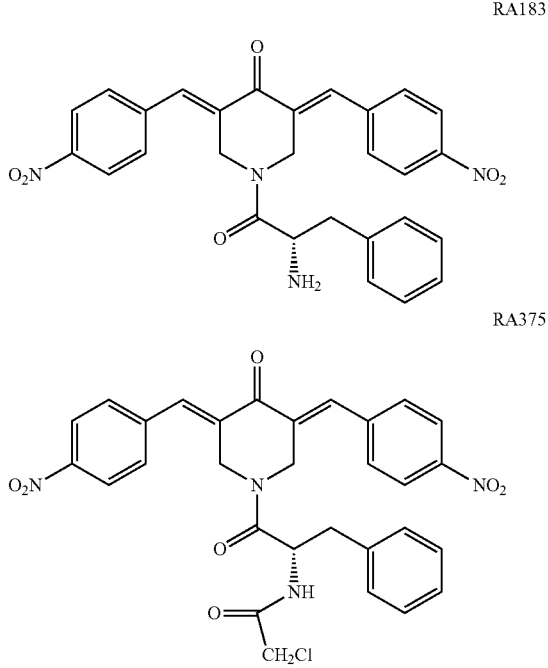

It was first sought to identify whether RA475 binds to RPN13. Since a biotin-tagged version of RA190 had previously been shown to bind covalently with the 42 kDa RPN13 protein in cell lysates, this chemical probe approach was used to develop an RPN13-binding competition assay.

Figure 2:
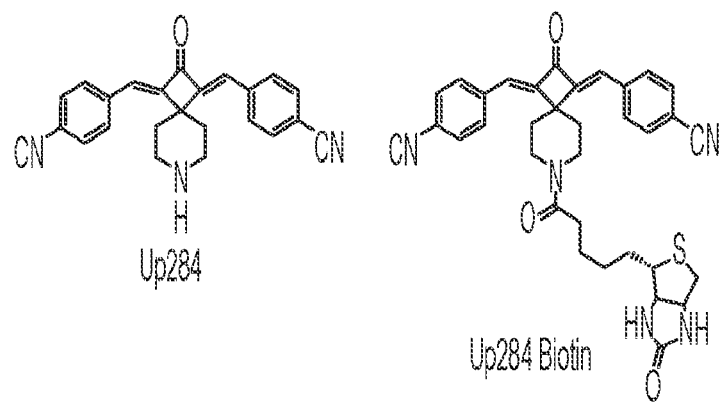
FIG. 2 shows the chemical structures of Up284 and Up284 Biotin (Up284B).

Unfortunately there is not a feasible site on RA475 to readily attach the biotin tag without disrupting the known pharmacophore. To confirm that the spiro-bis-benzylidine piperidone backbone binds covalently to RPN13 as seen for RA190, Up284 was utilized as the scaffold and Up284-biotin (Up284B) as the probe, because of its structural similarity to RA475 (FIG. 2).

ES2 cell lysates were incubated with 20 μM RA190B for 45 min at 4° C., and then separated by SDS-PAGE, transferred to a PVDF membrane. When the membrane was probed with streptavidin-HRP and its binding visualized using chemiluminesence, it was evident that RA190B bound to the 42 kDa cellular protein previously identified as RPN13. Pre-incubation of the lysate for 45 min at 4° C. with unlabeled RA190 competed with the binding of RA190B to the 42 kDa protein (positive control), whereas neither the vehicle (DMSO) nor bortezomib (negative controls) competed (FIG. 3A) demonstrating the validity of the competition assay. Pre-incubation of the lysate with 5 μM of the spiro-bis-benzylidine piperidone compounds Up104, Up109, Up284, Up285 and to a lesser extent Up111, all competed with binding of RA190B to the 42 kDa RPN13.

To confirm that Up284 is only binding detectably to the 42 kDa cellular protein previously identified as RPN13, ES2 cell lysate was incubated with titrated doses of RA190B (positive control), DMSO (negative control) or Up284B for 45 min at 4° C. The lysates were then separated by SDS-PAGE, transferred to a PVDF membrane. When the membrane was probed with streptavidin-HRP, it was evident based upon the titration and signal that Up284B bound to the same size 42 kDa cellular protein more avidly than RA190B (FIG. 3B). These data suggest that the spiro-bis-benzylidine piperidone Up284 binds covalently to RPN13 even more avidly than seen for RA190, and that the binding is highly specific.

RA475 Inhibits Proteasome Function

Figure 4:
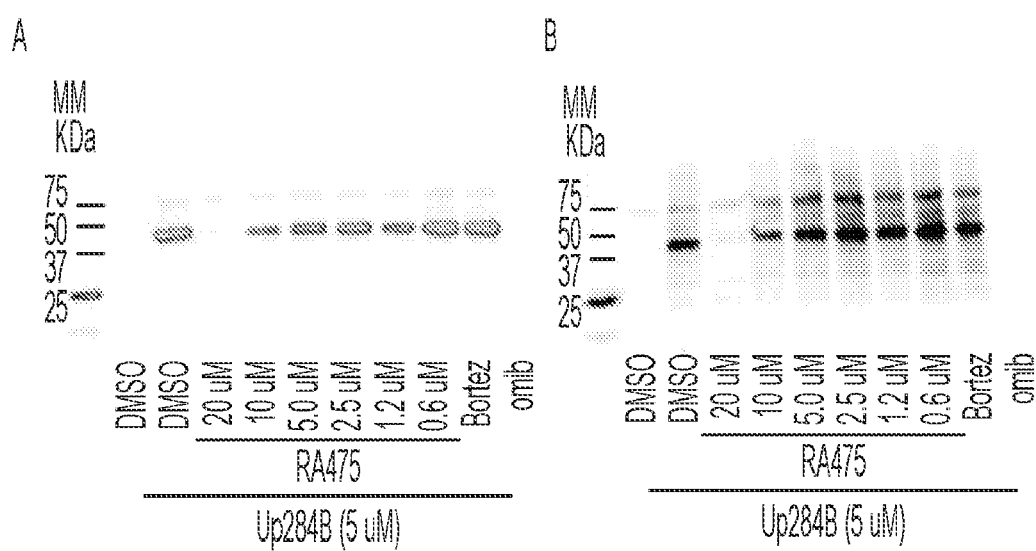
FIG. 4A shows RA475 competes with Up284B binding to a 42 kDa cellular protein, consistent with binding to RPN13, in ES2 cell lysate precleared with streptavidin-Dynabeads.
FIG. 4B shows RA475 competes with Up284B binding to a 42 kDa cellular protein, consistent with binding to RPN13, in SKOV3 cell lysate precleared with streptavidin-Dynabeads.

To examine whether RA475 also binds to RPN13, the labeling experiment was performed using Up284B as the RPN13-binding probe for lysate derived from two different ovarian cancers. Briefly SKOV3 or ES2 cell lysates were first pre-cleared with streptavidin-coated beads to deplete endogenous biotinylated proteins. The pre-cleared lysates were then divided into equal aliquots. Aliquots were each treated with titrations of RA475, or as negative controls bortezomib or the vehicle DMSO, for 45 min at 4° C., and then each was treated with 5 μM Up284B for a further 45 min at 4° C. The lysates were then boiled in gel sample buffer, separated by SDS-PAGE, and transferred to a PVDF membrane. The presence of the chemical probe for RPN13, Up284B, was visualized using streptavidin-HRP and chemiluminesence. Binding of Up284B to a 42 kDa cellular protein, consistent with RPN13, was detected. This was not competed by prior incubation with the 20S inhibitor bortezomib, as expected. Importantly, covalent binding of the Up284B probe to RPN13 is dose-dependently competed by pre-incubation with RA475 (FIG. 4).

It was examined whether the RPN13 inhibitor, RA475, was cytotoxic for cancer cell lines using the MTT assay. Sub micromolar IC50 values were observed for all solid cancer-derived cell lines tested. By contrast, the non-transformed human foreskin fibroblasts did not reach an IC50 at the highest concentration tested, 2.5 µM, suggestive of a significant therapeutic window.

TABLE 1

Cytotoxicity of RA475 against cell lines derived from several cancer types. Cell lines from different cancer types or human foreskin fibroblasts (HFF) were treated with titrations of RA475 and cultured for 72 hr. The cell viability was measured using standard MTT assay.
Cell killing assays of guanidine molecules (IC50 values mentioned in µM)

| Cell Line | Cancer type | RA475 | RA477 | RA479 | RA482 | RA484 |
|---|---|---|---|---|---|---|
| SKOV3 | ovarian | 0.19 | | | | |
| OVCAR3 | ovarian | 0.19 | | | | |
| ES2 | ovarian | 0.16 | | | | |
| SKOV3 | ovarian | 0.3 | | | | |
| PEO23 | ovarian | 0.35 | | | | |
| HeLa | cervical | 0.213 | | | | |
| BT549 | breast | 0.229 | | | | |
| SUM149 | breast | 0.10 | | | | |
| MCF7 | breast | 0.742 | | | | |
| HCC1806 | breast | 0.113 | | | | |
| MDA-MB-468 | breast | 0.292 | | | | |
| HepG2 | liver | 0.241 | | | | |
| MC38 | colon | 0.359 | | | | |
| DLD-1 | colon | 0.491 | | | | |
| HCT116 | colon | 0.43 | | | | |
| HFF | none | >2.5 | | | | |
| 4T1 | breast (TNBC) | 0.261 | | | | |
| TC1 | cervical | 0.217 | | | | |
| TSH1 | thyroid | 0.114 | | | | |
| PACS | ovarian (mouse) | 0.581 | 0.405 | | | |
| PEA1 | ovarian | 0.406 | 0.331 | 0.35 | 0.396 | 0.479 |
| PEA2 | ovarian | 0.356 | 0.312 | 0.32 | 0.41 | 0.522 |
| U251MG | glioblastoma multiforme | 0.6 | | | | |
| Br23C | glioblastoma multiforme | 0.75 | | | | |

Like RA190, RA475 was designed to be an inhibitor of upstream 19S RP proteasome function. Therefore, it was examined whether RA475 treatment induced a rapid accumulation of high molecular weight polyubiqutinated proteins (polyUb), presumably by preventing their degradation. Ovarian cancer-derived SKOV3 cells were treated with RA475 at just above and three times the IC50 (Table 1) and incubated for 12 hr. Treatment with the same doses of Up284 (0.5 and 1 µM) or 1 µM RA190 provided positive controls, and vehicle alone (DMSO) was used as the negative control. At the end of the incubation, attached cells were lysed using MPER buffer according to the manufacturer's protocol. The lysates were subjected to Western blot analysis using antibody to ubiquitin, and then stripped and re-probed with actin antibody to provide a loading control (FIG. 5). Both the positive control compounds, RA190 and Up284, showed profound accumulation of polyUb proteins, and RA475 likewise induced a very significant increase in a dose-dependent manner.

RA475 Causes Apoptotic Cell Death

Proteasome inhibitors cause a rapid accumulation of polyUb proteins that is associated with unresolved UPR stress and the induction of apoptosis. Since RA475 is cytotoxic to ovarian cancer cells (Table 1), and induces such a rapid accumulation of polyUb proteins (FIG. 5), it was examined whether RA475 also triggered apoptosis. SKOV3 cells (FIG. 5A) were treated with Up284 (0.5 µM and 1 µM), 1 µM RA190, RA475 (0.5 µM and 1 µM) or vehicle alone (DMSO) and then cultured for 12 hr. OVCAR3 cells (FIG. 5B) were treated with Up284 (0.5 µM), Bortezomib (Bz, 0.25 µM), Ixazomib (Iz, 0.25 µM), RA475 (0.5 µM and 1 µM) or vehicle alone (DMSO). The attached cells were harvested and their lysates were subjected to Western blot analysis, first probed with antibody to ubiquitin and then to actin.

Two ovarian cancer cell lines, ES2 and OVCAR3, were treated with 1 µM or 2 µM RA475 and 16 hr later the cells were harvested and stained with 7-AAD and Annexin V. 7-AAD is a DNA dye that can enter dying cells and Annexin V is commonly used to detect apoptotic cells by its ability to bind to phosphatidylserine, an early marker of apoptosis when it is exposed on the outer leaflet of the plasma membrane. Flow cytometric analysis showed a dose-dependent induction of 7-AAD and Annexin V double positive cells after treatment with RA475 (FIG. 6).

RA475 is Stable in Plasma and Liver Microsomes of Both Murine and Human Origin

As a prelude to in vivo studies with RA475, first examined was its stability in plasma and liver microsomes of both murine and human origin (Tables 2 and 3). Upon incubation with EDTA-treated murine and human plasma for 1 hr at 37° C., RA475 was metabolically stable since all alterations in the area ratios were well within typical analytical variability allowance (15%). In plasma and neat solution, there was no decrease in the ratio. A maximal decrease of 7% was observed in human liver microsomes lacking NADPH regeneration solution. By contrast, RA190 and RA183 were rapidly metabolized under these conditions (34). Up284 is more stable that RA190 and RA183, but less so than RA475 in biological matrices (Table 4). Interestingly, a large portion of Up284 exhibited non-enzymatic (NADPH negative; ~50%) degradation compared to CYP450 activity (NADPH positive) which added only an additional 9-13% degradation (Table 5).

TABLE 2

Stability of RA475 in murine and human plasma.

| Stability Matrix Time (minutes) | Neat Solution % Drug Remaining | Plasma (Mouse EDTA) % Drug Remaining | Plasma (Human EDTA) % Drug Remaining |
|---|---|---|---|
| 0 | 100% | 100% | 100% |
| 30 | 108% | 109% | 108% |
| 60 | 111% | 109% | 107% |

TABLE 3

Stability of RA475 in murine and human liver microsomes, with or without exogenous NADPH.

| | Mouse Liver Microsomes | | Human Liver Microsomes | |
|---|---|---|---|---|
| Stability Matrix Time (minutes) | % Drug Remaining NADPH Neg | % Drug Remaining NADPH Pos | % Drug Remaining NADPH Neg | % Drug Remaining NADPH Pos |
| 0 | 100% | 100% | 100% | 100% |
| 30 | 90% | 93% | 99% | 112% |
| 60 | 108% | 98% | 93% | 102% |

TABLE 4

Stability of Up284 in murine and human plasma.

| Stability Matrix Time (minutes) | Neat Solution % Drug Remaining | Plasma (Mouse EDTA) % Drug Remaining | Plasma (Human EDTA) % Drug Remaining |
|---|---|---|---|
| 0 | 100% | 100% | 100% |
| 30 | 86% | 84% | 100% |
| 60 | 78% | 94% | 90% |

TABLE 5

Stability of Up284 in murine and human liver microsomes, with or without exogenous NADPH.

| | Mouse Liver Microsomes | | Human Liver Microsomes | |
|---|---|---|---|---|
| Stability Matrix Time (minutes) | % Drug Remaining NADPH Neg | % Drug Remaining NADPH Pos | % Drug Remaining NADPH Neg | % Drug Remaining NADPH Pos |
| 0 | 100% | 100% | 100% | 100% |
| 30 | 60% | 45% | 57% | 43% |
| 60 | 51% | 38% | 52% | 43% |

RA475 Treatment is Tolerated by Mice with NOAEL>80 mg/kg Fora Single Dose

RA475 powder was directly dissolved in 25% β-hydroxy propyl cyclodextrin as a clear solution and administered at increasing single doses to CD-1 mice (n=3) via intraperitoneal injection. No evidence of adverse events, including weight loss, was detected at or below 80 mg/Kg of animal weight, the highest dose level tested.

RA475 Inhibited Proteasomal Degradation of 4UbFL Reporter in Cells and Mice

To measure RA475 on-target activity in live cells, the inventors used an expression vector for the reporter gene 4UbFL in which the gene for firefly luciferase (FL) is inserted in-frame 3' to four copies of ubiquitin (PMID: 12819780). Whereas wild type FL protein is highly stable, the 4UbFL protein is rapidly degraded by the 26S proteasome. Proteasome inhibition stabilizes 4UbFL and thus increases the bioluminescence signal upon addition of luciferin substrate, and this can be measured by a luminometer (for cells) or visualized by IVIS imaging (for mice).

ES2 cells stably transfected with 4UbFL expression plasmid (ES2-4UbFL) were plated in a 96 well microtiter plate and 18 hr later treated with DMSO only as a negative control, or two-fold dilution series of either Up284 or RA475. After 4 hr medium was removed and the cells were lysed using luciferase lysis buffer and bioluminescence was measured using a luminometer after the addition of luciferin substrate. Both Up284 and RA475 significantly increased the bioluminescent signal in a very similar dose-dependent manner, although signal dropped off at the highest doses, likely reflecting the onset of cell death (FIG. 7A). This suggests similar on-target potency for Up284 and RA475 in live cells.

To assess on-target activity in vivo, 4UbFL plasmid was injected into the muscle of one leg of CD-1 mice followed by electroporation. Luciferin was injected i.p. 24 hr later and the mice were tagged and imaged using an IVIS200 to visualize their basal bioluminescence. The mice were then immediately randomized to 3 groups and treated with vehicle alone (25% β-hydroxypropylcyclodextrin-water solution), RA475 (40 mg/Kg) and Up284 (40 mg/Kg) administered as a single i.p. dose. To examine the on-target activity, the mice were imaged again at 4 hr, 24 hr, 48 hr, 72 hr and 96 hr later. A 24-fold increase in bioluminescence at the site of electroporation was observed at 4 hr after administration of RA475 (FIG. 7B) and 6-fold at 24 hr, whereas Up284 induced a weaker response of ~3-fold that peaked at 24 hr post-administration. This pharmacodynamic data suggests that the RA475 more readily exits the peritoneal cavity than Up284, and enters the leg muscle via peripheral circulation given their similar activity in the cell line.

RA475 Stabilized Proteasome Reporter in Cells

Figure 8:
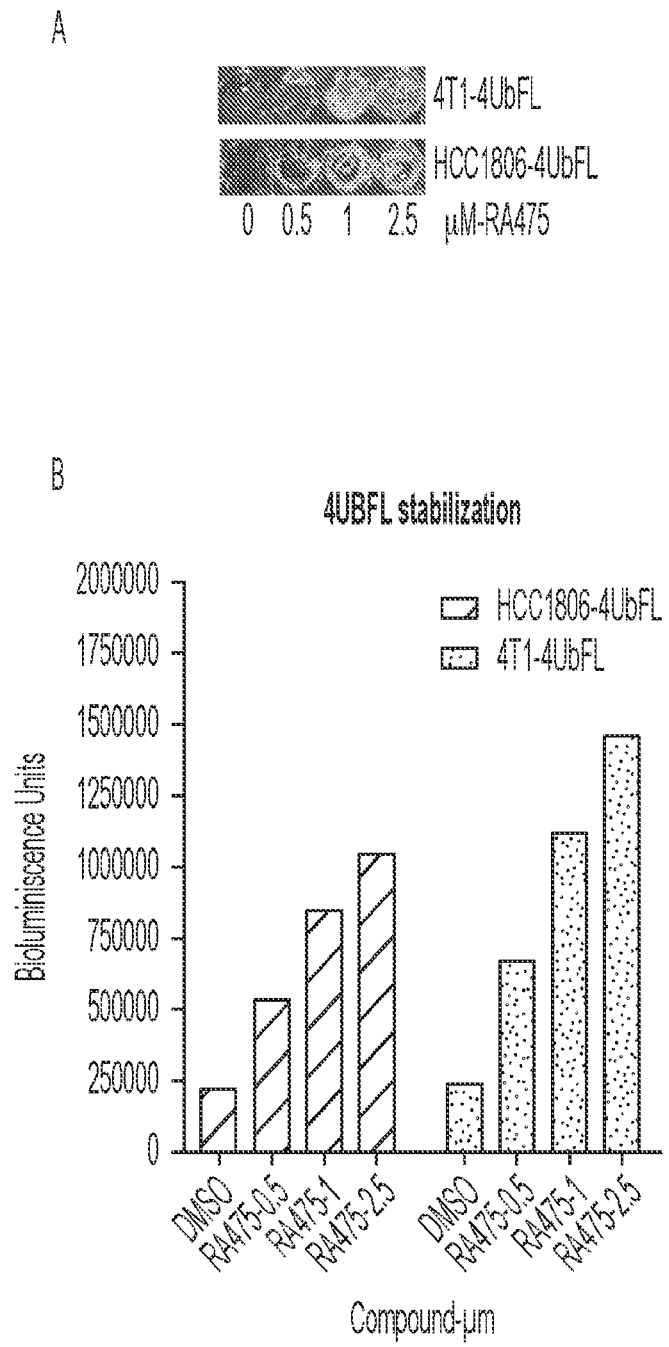
FIG. 8A shows IVIS images of 4T1 and HCC1806 cells stably expressing 4UbFL 4 hr after treatment with RA475.
FIG. 8B shows the bioluminescence units of 4T1 and HCC1806 cells stably expressing 4UbFL 4 hr after treatment with RA475.

4T1 and HCC1806 cells stably expressing 4UbFL show a dose-dependent increase in bioluminescence after 4 hr treatment with RA475 as measured by IVIS imager. Data are presented as IVIS image (FIG. 8A) and bioluminescence units (FIG. 8B).

4T1 and HCC1806 cells were transfected with 4UbFL plasmid using TransIT2020 transfection reagent for a period of 48 hrs and cells were selected using G418 antibiotic from single colonies. Selected cells were seeded in a 24-well plate (50,000/well) and incubated for 18 h at 37° C. in an incubator. Next, cells were treated with compounds for the period of 4 hr and Luciferin was added (50 uL each well, 7.8 mg/mL) and imaged through an IVIS200 instrument and plotted as a bioluminescent value or fold increase to DMSO control.

RA475 Oral Bioavailability and On-Target Activity in Mice

Figure 9:
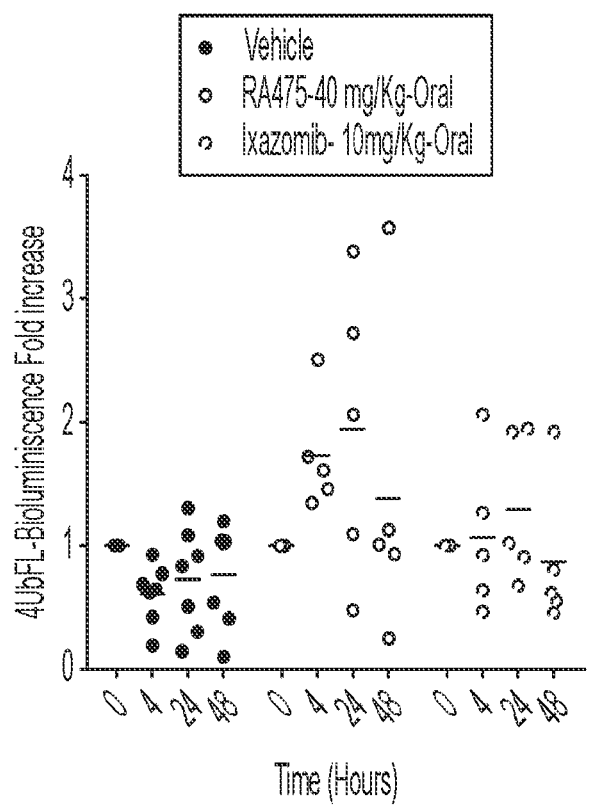
FIG. 9 shows the oral bioavailability and on-target activity of RA475 in mice.

CD-1 mice were electroporated after injection of the 4UbFL plasmid into the muscle of one leg and tagged. Administration of luciferin substrate i.p. and IVIS200 imaging of the mice at the site of 4UbFL plasmid injection was performed 24 hr after electroporation. This time point was considered baseline. Mice were then randomized into three groups and treated with vehicle alone (n=7, 25% β-hydroxypropylcyclodextrin-water solution), RA475 (n=5, 40 mg/Kg) and Ixazomib (n=5, 10 mg/Kg/) administered as a single oral dose. The mice were imaged again at 4 hr, 24 hr, 48 hr later. Data are presented as fold increase over bioluminescence of injection site at baseline for individual mice followed longitudinally (FIG. 9).

RA475 Regressed Ovarian Tumor in a Syngeneic Model

Figure 10:
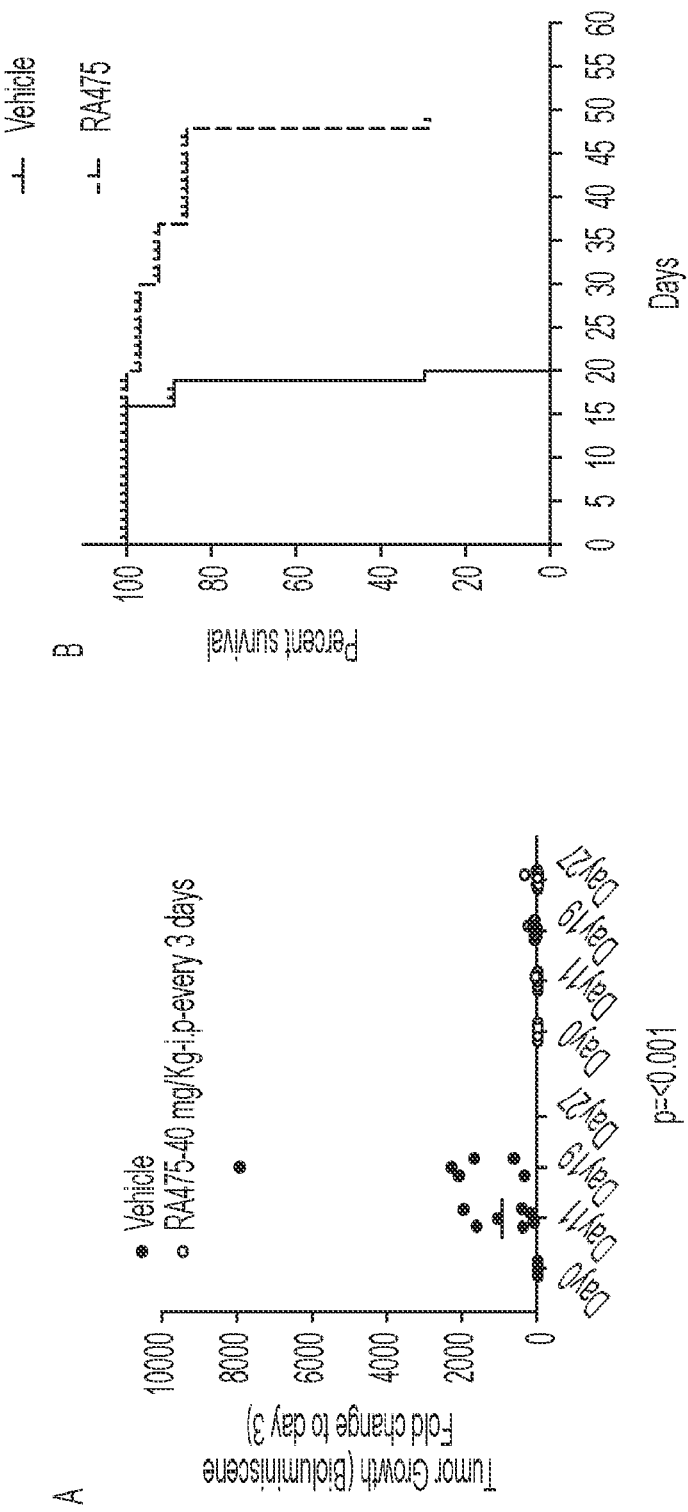
FIG. 10 shows RA475 regressed ovarian tumors in a syngeneic mouse model.
Figure 10:
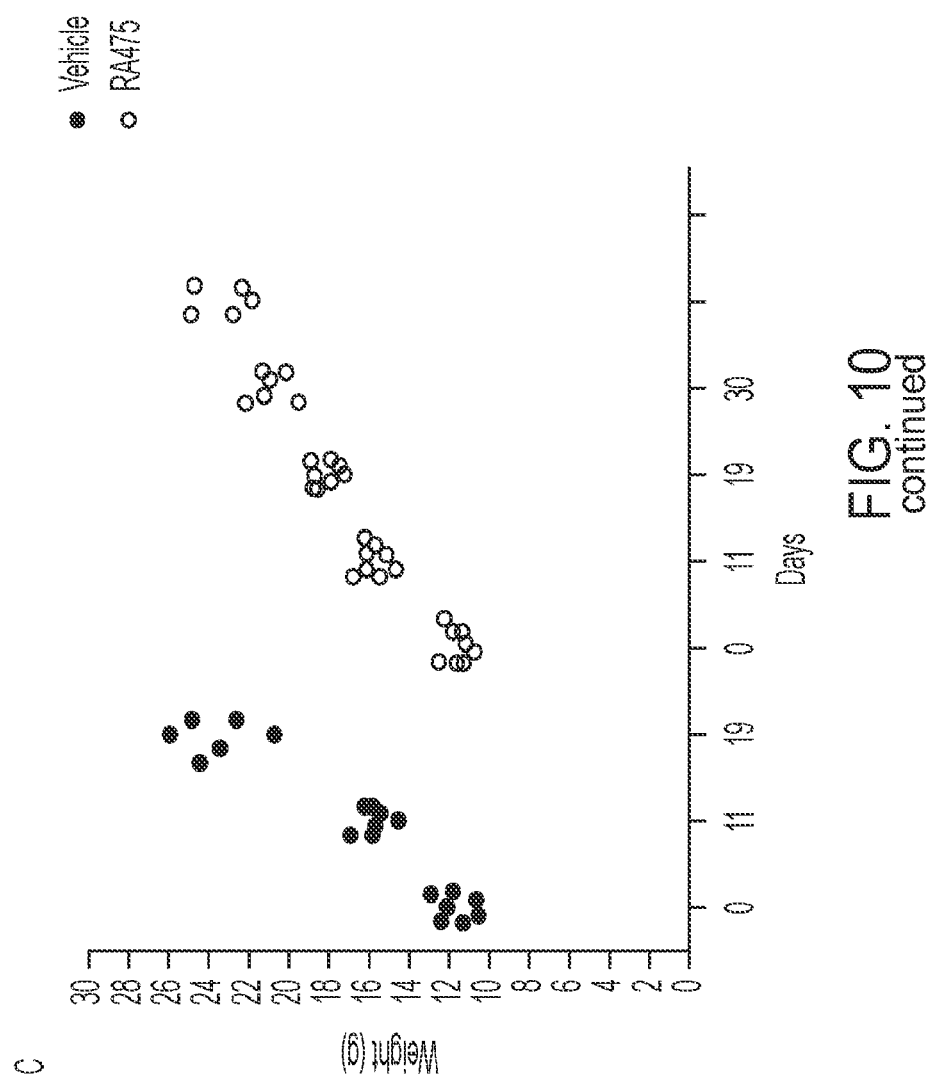

Female C57BL6 mice bearing ID8-Lu tumor show tumor control (FIG. 10A); survival (FIG. 10 B); and no weight loss (FIG. 10C) with RA475 (40 mg/Kg every 3 days, i.p) treatment (n=8). Whereas vehicle treatment (n=7) increased tumor burden and ascites formation.

Briefly, female C57BL6 mice were injected (i.p.) with ID8-Vegf Defb29 cells stably expressing firefly luciferase ($0.5 \times 10^6$ cells) in PBS (100 uL). After 72 hrs, mice were imaged for their basal luminescence levels using an IVIS200 imager. Mice with visible luminescence were randomized into two groups and treated with Vehicle (25% b-hydroxy propylcyclodextrin in water, 200 uL, every 3 days, i.p.) and RA475 (40 mg/Kg, every 3 days, i.p.). Mice were imaged every week to measure bioluminescence expressed by tumor after administration of luciferin (100 uL, 7.8 mg/mL). In the vehicle group all 7 mice showed enlarged abdomens due to ascites formation. Whereas RA475 treatment regressed tumor and enhanced survival.

REFERENCES

1. Budenholzer L, Cheng C L, Li Y, Hochstrasser M. 2017. Proteasome Structure and Assembly. J Mol Biol 429: 3500-3524.
2. Collins G A, Goldberg A L. 2017. The Logic of the 26S Proteasome. Cell 169:792-806.
3. Cromm P M, Crews C M. 2017. The Proteasome in Modern Drug Discovery: Second Life of a Highly Valuable Drug Target. ACS Cent Sci 3:830-838.
4. Xi J, Zhuang R, Kong L, He R, Zhu H, Zhang J. 2019. Immunoproteasome-selective inhibitors: An overview of recent developments as potential drugs for hematologic malignancies and autoimmune diseases. Eur J Med Chem 182:111646.
5. Bazzaro M, Lee M K, Zoso A, Stirling W L, Santillan A, Shih le M, Roden R B. 2006. Ubiquitin-proteasome system stress sensitizes ovarian cancer to proteasome inhibitor-induced apoptosis. Cancer Res 66:3754-3763.
6. Yu J, Tiwari S, Steiner P, Zhang L. 2003. Differential apoptotic response to the proteasome inhibitor Bortezomib [VELCADE, PS-341] in Bax-deficient and p21-deficient colon cancer cells. Cancer Biol Ther 2:694-699.
7. Petrocca F, Altschuler G, Tan S M, Mendillo M L, Yan H, Jerry D J, Kung A L, Hide W, Ince T A, Lieberman J. 2013. A genome-wide siRNA screen identifies proteasome addiction as a vulnerability of basal-like triple-negative breast cancer cells. Cancer Cell 24:182-196.
8. Tsvetkov P, Adler J, Myers N, Biran A, Reuven N, Shaul Y. 2018. Oncogenic addiction to high 26S proteasome level. Cell Death Dis 9:773.
9. Parma G, Mancari R, Del Conte G, Scambia G, Gadducci A, Hess D, Katsaros D, Sessa C, Rinaldi A, Bertoni F, Vitali A, Catapano C V, Marsoni S, van de Velde H, Colombo N. 2012. An open-label phase 2 study of twice-weekly bortezomib and intermittent pegylated liposomal doxorubicin in patients with ovarian cancer failing platinum-containing regimens. Int J Gynecol Cancer 22:792-800.
10. Adelson K, Ramaswamy B, Sparano J A, Christos P J, Wright J J, Raptis G, Han G, Villalona-Calero M, Ma C X, Hershman D, Baar J, Klein P, Cigler T, Budd G T, Novik Y, Tan A R, Tannenbaum S, Goel A, Levine E, Shapiro C L, Andreopoulou E, Naughton M, Kalinsky K, Waxman S, Germain D. 2016. Randomized phase II trial of fulvestrant alone or in combination with bortezomib in hormone receptor-positive metastatic breast cancer resistant to aromatase inhibitors: a New York Cancer Consortium trial. NPJ Breast Cancer 2:16037.
11. Pugh T J, Chen C, Rabinovitch R, Eckhardt S G, Rusthoven K E, Swing R, Raben D. 2010. Phase I trial of bortezomib and concurrent external beam radiation in patients with advanced solid malignancies. Int J Radiat Oncol Biol Phys 78:521-526.
12. Gilbert J, Lee J W, Argiris A, Haigentz M, Jr., Feldman L E, Jang M, Arun P, Van Waes C, Forastiere A A. 2013. Phase II 2-arm trial of the proteasome inhibitor, PS-341 (bortezomib) in combination with irinotecan or P5-341 alone followed by the addition of irinotecan at time of progression in patients with locally recurrent or metastatic squamous cell carcinoma of the head and neck (E1304): a trial of the Eastern Cooperative Oncology Group. Head Neck 35:942-948.
13. Jandial D A, Brady W E, Howell S B, Lankes H A, Schilder R J, Beumer J H, Christner S M, Strychor S, Powell M A, Hagemann A R, Moore K N, Walker J L, DiSilvestro P A, Duska L R, Fracasso P M, Dizon D S. 2017. A phase I pharmacokinetic study of intraperitoneal bortezomib and carboplatin in patients with persistent or recurrent ovarian cancer: An NRG Oncology/Gynecologic Oncology Group study. Gynecol Oncol 145:236-242.
14. Roeten M S F, Cloos J, Jansen G. 2018. Positioning of proteasome inhibitors in therapy of solid malignancies. Cancer Chemother Pharmacol 81:227-243.
15. Dou Q P, Zonder J A. 2014. Overview of proteasome inhibitor-based anti-cancer therapies: perspective on bortezomib and second generation proteasome inhibitors versus future generation inhibitors of ubiquitin-proteasome system. Curr Cancer Drug Targets 14:517-536.
16. Shi Y, Chen X, Elsasser S, Stocks B B, Tian G, Lee B H, Shi Y, Zhang N, de Poot S A, Tuebing F, Sun S, Vannoy J, Tarasov S G, Engen J R, Finley D, Walters K J. 2016. Rpn1 provides adjacent receptor sites for substrate binding and deubiquitination by the proteasome. Science 351.
17. Elsasser S, Chandler-Militello D, Muller B, Hanna J, Finley D. 2004. Rad23 and Rpn10 serve as alternative ubiquitin receptors for the proteasome. J Biol Chem 279:26817-26822.
18. Husnjak K, Elsasser S, Zhang N, Chen X, Randles L, Shi Y, Hofmann K, Walters K J, Finley D, Dikic I. 2008. Proteasome subunit Rpn13 is a novel ubiquitin receptor. Nature 453:481-488.
19. Lu X, Ebelle D L, Matsuo H, Walters K J. 2020. An Extended Conformation for K48 Ubiquitin Chains Revealed by the hRpn2:Rpn13:K48-Diubiquitin Structure. Structure doi:10.1016/j.str.2020.02.007.
20. Cundiff M D, Hurley C M, Wong J D, Boscia J At, Bashyal A, Rosenberg J, Reichard E L, Nassif N D, Brodbelt J S, Kraut D A. 2019. Ubiquitin receptors are required for substrate-mediated activation of the proteasome's unfolding ability. Sci Rep 9:14506.
21. Martinez-Fonts K, Davis C, Tomita T, Elsasser S, Nager A R, Shi Y, Finley D, Matouschek A. 2020. The proteasome 19S cap and its ubiquitin receptors provide a versatile recognition platform for substrates. Nat Commun 11:477.

22. Chen X, Walters K J. 2015. Structural plasticity allows UCH37 to be primed by RPN13 or locked down by INO80G. Mol Cell 57:767-768.
23. Vander Linden R T, Hemmis C W, Schmitt B, Ndoja A, Whitby F G, Robinson H, Cohen R E, Yao T, Hill C P. 2015. Structural basis for the activation and inhibition of the UCH37 deubiquitylase. Mol Cell 57:901-911.
24. Jiao L, Ouyang S, Shaw N, Song G, Feng Y, Niu F, Qiu W, Zhu H, Hung L W, Zuo X, Eleonora Shtykova V, Zhu P, Dong Y H, Xu R, Liu Z J. 2014. Mechanism of the Rpn13-induced activation of Uch37. Protein Cell 5:616-630.
25. VanderLinden R T, Hemmis C W, Yao T, Robinson H, Hill C P. 2017. Structure and energetics of pairwise interactions between proteasome subunits RPN2, RPN13, and ubiquitin clarify a substrate recruitment mechanism. J Biol Chem 292:9493-9504.
26. Chen X, Lee B H, Finley D, Walters K J. 2010. Structure of proteasome ubiquitin receptor hRpn13 and its activation by the scaffolding protein hRpn2. Mol Cell 38:404-415.
27. Hemmis C W, Heard S C, Hill C P. 2019. Phosphorylation of Tyr-950 in the proteasome scaffolding protein RPN2 modulates its interaction with the ubiquitin receptor RPN13. J Biol Chem 294:9659-9665.
28. Lu X, Liu F, Durham S E, Tarasov S G, Walters K J. 2015. A High Affinity hRpn2-Derived Peptide That Displaces Human Rpn13 from Proteasome in 293T Cells. PLoS One 10:e0140518.
29. Besche H C, Sha Z, Kukushkin N V, Peth A, Hock E M, Kim W, Gygi S, Gutierrez J A, Liao H, Dick L, Goldberg A L. 2014. Autoubiquitination of the 26S proteasome on Rpn13 regulates breakdown of ubiquitin conjugates. EMBO J 33:1159-1176.
30. Jiang R T, Yemelyanova A, Xing D, Anchoori R K, Hamazaki J, Murata S, Seidman J D, Wang T L, Roden RBS. 2017. Early and consistent overexpression of ADRM1 in ovarian high-grade serous carcinoma. J Ovarian Res 10:53.
31. Soong R S, Anchoori R K, Yang B, Yang A, Tseng S H, He L, Tsai Y C, Roden R B, Hung C F. 2016. RPN13/ADRM1 inhibitor reverses immunosuppression by myeloid-derived suppressor cells. Oncotarget 7:68489-68502.
32. Fejzo M S, Anderson L, Chen H W, Anghel A, Zhuo J, Anchoori R, Roden R, Slamon D J. 2015. ADRM1-amplified metastasis gene in gastric cancer. Genes Chromosomes Cancer 54:506-515.
33. Jang S H, Park J W, Kim H R, Seong J K, Kim H K. 2014. ADRM1 gene amplification is a candidate driver for metastatic gastric cancers. Clin Exp Metastasis 31:727-733.
34. Anchoori R K, Karanam B, Peng S, Wang J W, Jiang R, Tanno T, Orlowski R Z, Matsui W, Zhao M, Rudek M A, Hung C F, Chen X, Walters K J, Roden R B. 2013. A bis-benzylidine piperidone targeting proteasome ubiquitin receptor RPN13/ADRM1 as a therapy for cancer. Cancer Cell 24:791-805.
35. Kisselev A F. 2013. A novel bullet hits the proteasome. Cancer Cell 24:691-693.
36. Fejzo M S, Anderson L, von Euw E M, Kalous O, Avliyakulov N K, Haykinson M J, Konecny G E, Finn R S, Slamon D J. 2013. Amplification Target ADRM1: Role as an Oncogene and Therapeutic Target for Ovarian Cancer. Int J Mol Sci 14:3094-3109.
37. Hamazaki J, Hirayama S, Murata S. 2015. Redundant Roles of Rpn10 and Rpn13 in Recognition of Ubiquitinated Proteins and Cellular Homeostasis. PLoS Genet 11:e1005401.
38. Al-Shami A, Jhaver K G, Vogel P, Wilkins C, Humphries J, Davis J J, Xu N, Potter D G, Gerhardt B, Mullinax R, Shirley C R, Anderson S J, Oravecz T. 2010. Regulators of the proteasome pathway, Uch37 and Rpn13, play distinct roles in mouse development. PLoS One 5:e13654.
39. Zheng X, Guo Y, Chen Y, Chen M, Lin Z, Wu Y, Chen Y. 2015. Knockdown of Adhesion-Regulating Molecule 1 Inhibits Proliferation in HL60 Cells. Acta Haematol 134: 88-100.
40. Fejzo M S, Dering J, Ginther C, Anderson L, Ramos L, Walsh C, Karlan B, Slamon D J. 2008. Comprehensive analysis of 20q13 genes in ovarian cancer identifies ADRM1 as amplification target. Genes Chromosomes Cancer 47:873-883.
41. Baell J B, Nissink J W M. 2018. Seven Year Itch: Pan-Assay Interference Compounds (PAINS) in 2017- Utility and Limitations. ACS Chem Biol 13:36-44.
42. Lagorce D, Oliveira N, Miteva M A, Villoutreix B O. 2017. Pan-assay interference compounds (PAINS) that may not be too painful for chemical biology projects. Drug Discov Today 22:1131-1133.
43. Rowinsky E K, Paner A, Berdeja J G, Paba-Prada C, Venugopal P, Porkka K, Gullbo J, Linder S, Loskog A, Richardson P G, Landgren O. 2020. Phase 1 study of the protein deubiquitinase inhibitor VLX1570 in patients with relapsed and/or refractory multiple myeloma. Invest New Drugs doi:10.1007/s10637-020-00915-4.
44. Zheng Y J, Tice C M. 2016. The utilization of spirocyclic scaffolds in novel drug discovery. Expert Opin Drug Discov 11:831-834.
45. Muller G, Berkenbosch T, Benningshof J C, Stumpfe D, Bajorath J. 2017. Charting Biologically Relevant Spirocyclic Compound Space. Chemistry 23:703-710.
46. Luker G D, Pica C M, Song J, Luker K E, Piwnica-Worms D. 2003. Imaging 26S proteasome activity and inhibition in living mice. Nat Med 9:969-973.
47. Daina A, Michielin O, Zoete V. 2017. SwissADME: a free web tool to evaluate pharmacokinetics, drug-likeness and medicinal chemistry friendliness of small molecules. Sci Rep 7:42717.
48. Yang J J, Ursu O, Lipinski C A, Sklar L A, Oprea T I, Bologa C G. 2016. Badapple: promiscuity patterns from noisy evidence. J Cheminform 8:29.
49. Dahlin J L, Walters M A. 2016. How to Triage PAINS-Full Research. Assay Drug Dev Technol 14:168-174.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

The invention claimed is:

1. A compound selected from the group consisting of,

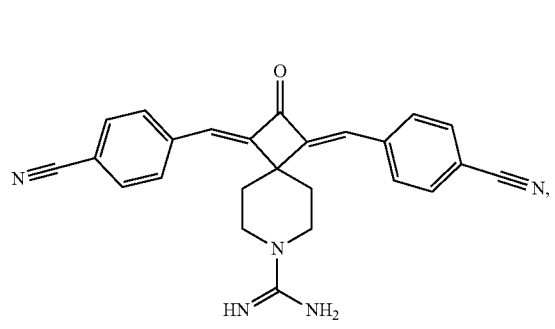

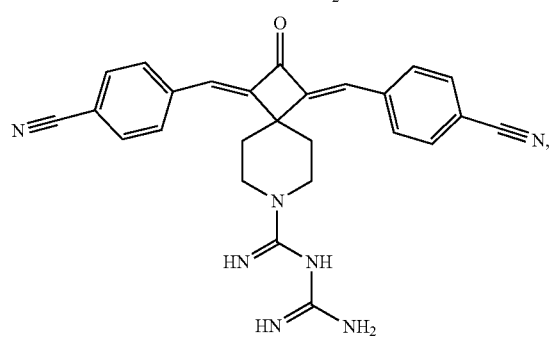

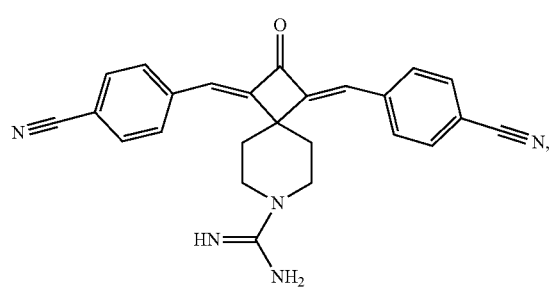

RA477

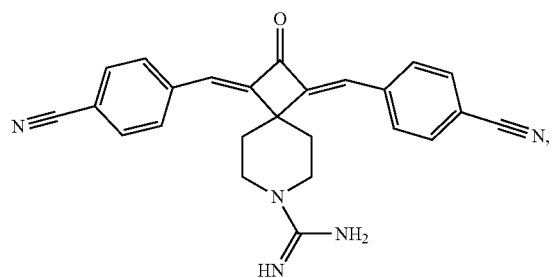

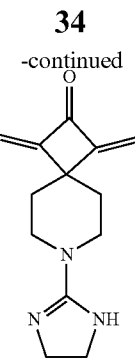

-continued

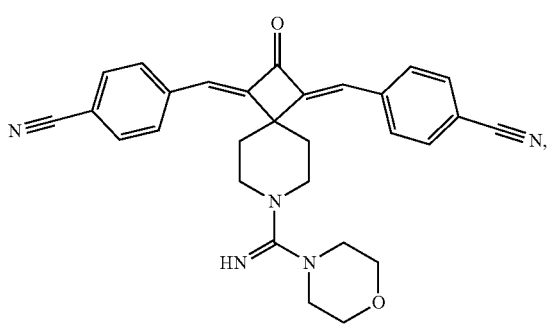

RA484

RA479

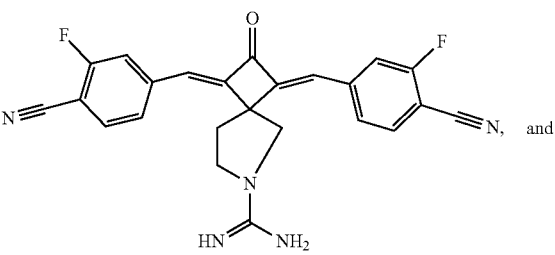

and

RA482

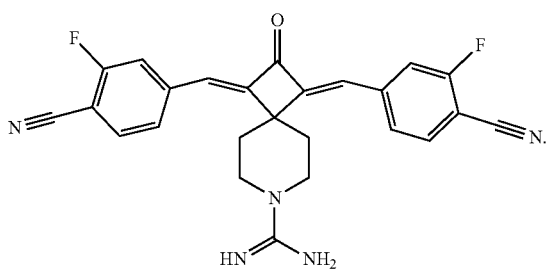

2. A method of treating cancer comprising administering a compound of claim 1, wherein the cancer is selected from the group consisting of multiple myeloma, ovarian cancer, cervical cancer, breast cancer, liver cancer, and colon cancer.

3. The method of claim 2, wherein the cancer is a liquid cancer or a solid cancer.

4. The method of claim 3 wherein the cancer is a solid cancer.

* * * * *